(12) United States Patent
Greener (10) Patent No.: US 9,962,474 B2
(45) Date of Patent: May 8, 2018

(54) VACUUM ASSISTED WOUND DRESSING

(71) Applicant: Smith & Nephew PLC, London (GB)

(72) Inventor: Bryan Greener, York (GB)

(73) Assignee: Smith & Nephew PLC, London (GB)

( * ) Notice: Subject to any disclaimer, the term of this patent is extended or adjusted under 35 U.S.C. 154(b) by 882 days.

(21) Appl. No.: 14/254,807

(22) Filed: Apr. 16, 2014

(65) Prior Publication Data

US 2014/0236109 A1 Aug. 21, 2014

Related U.S. Application Data

(63) Continuation of application No. 12/744,055, filed as application No. PCT/GB2008/051088 on Nov. 20, 2008, now Pat. No. 8,715,256.

(30) Foreign Application Priority Data

Nov. 21, 2007 (GB) .................................. 0722820.8

(51) Int. Cl.
| | | |
|---|---|---|
| A61F 13/00 | (2006.01) | |
| A61M 1/00 | (2006.01) | |
| A61M 39/24 | (2006.01) | |
| A61F 13/02 | (2006.01) | |

(52) U.S. Cl.
CPC ..... *A61M 1/0092* (2014.02); *A61F 13/00068* (2013.01); *A61F 13/0206* (2013.01); *A61F 13/0209* (2013.01); *A61F 13/0216* (2013.01); *A61F 13/0226* (2013.01); *A61M 1/0088* (2013.01); *A61F 2013/0094* (2013.01); *A61F 2013/00536* (2013.01); *A61M 1/0049* (2013.01); *A61M 39/24* (2013.01)

(58) Field of Classification Search
CPC combination set(s) only.
See application file for complete search history.

(56) References Cited

U.S. PATENT DOCUMENTS

| | | |
|---|---|---|
| 695,270 A | 3/1902 | Beringer |
| 1,480,562 A | 1/1924 | Mock |
| 2,280,915 A | 4/1942 | Johnson |

(Continued)

FOREIGN PATENT DOCUMENTS

| | | |
|---|---|---|
| CA | 2 198 243 | 2/1996 |
| CA | 2 367 460 | 10/2000 |

(Continued)

OTHER PUBLICATIONS

US 6,216,701, 04/2001, Heaton et al. (withdrawn)

(Continued)

*Primary Examiner* — Todd J Scherbel
*Assistant Examiner* — Guy K Townsend
(74) *Attorney, Agent, or Firm* — Knobbe, Martens, Olson & Bear LLP (57) ABSTRACT

Apparatus for the application of topical negative pressure therapy to a wound site is described, the apparatus comprising: a wound contacting element for retaining wound exudate fluid therein; a wound covering element that provides a substantially airtight seal over the wound contacting element and wound site; a vacuum connection tube connecting a wound cavity to a vacuum source; and a vacuum source connected to a distal end of the vacuum connection tube.

22 Claims, 3 Drawing Sheets

(56) References Cited

U.S. PATENT DOCUMENTS

| | | | |
|---|---|---|---|
| 2,367,690 | A | 7/1943 | Purdy |
| 2,568,933 | A | 9/1951 | Robbins |
| 2,632,443 | A | 3/1953 | Lesher |
| 2,682,873 | A | 7/1954 | Evans et al. |
| 2,910,763 | A | 8/1955 | Lauterbach |
| 3,115,138 | A | 12/1963 | McElvenny et al. |
| 3,367,332 | A | 2/1968 | Groves |
| 3,486,504 | A | 12/1969 | Austin, Jr. |
| 3,572,340 | A | 3/1971 | Lloyd et al. |
| 3,610,238 | A | 10/1971 | Rich, Jr. |
| 3,874,387 | A | 4/1975 | Barbieri |
| 3,972,328 | A | 8/1976 | Chen |
| 3,993,080 | A | 11/1976 | Loseff |
| 4,029,598 | A | 6/1977 | Neisius et al. |
| RE29,319 | E | 7/1977 | Nordby et al. |
| 4,102,342 | A | 7/1978 | Akiyama et al. |
| 4,112,947 | A | 9/1978 | Nehring |
| 4,136,696 | A | 1/1979 | Nehring |
| 4,184,510 | A | 1/1980 | Murry et al. |
| 4,217,894 | A | 8/1980 | Franetzki |
| 4,219,019 | A | 8/1980 | Coates |
| 4,224,945 | A | 9/1980 | Cohen |
| 4,250,882 | A | 2/1981 | Adair |
| 4,316,466 | A | 2/1982 | Babb |
| 4,382,441 | A | 5/1983 | Svedman |
| 4,465,485 | A | 8/1984 | Kashmer et al. |
| 4,468,227 | A | 8/1984 | Jensen |
| 4,525,166 | A | 6/1985 | Leclerc |
| 4,534,356 | A | 8/1985 | Papadakis |
| 4,551,141 | A | 11/1985 | McNeil |
| 4,573,965 | A | 3/1986 | Russo |
| 4,608,041 | A | 8/1986 | Nielsen |
| 4,655,754 | A | 4/1987 | Richmond et al. |
| 4,655,766 | A | 4/1987 | Theeuwes et al. |
| 4,681,562 | A | 7/1987 | Beck et al. |
| 4,710,165 | A | 12/1987 | McNeil et al. |
| 4,778,446 | A | 10/1988 | Jensen |
| 4,778,456 | A | 10/1988 | Lokken |
| 4,792,328 | A | 12/1988 | Beck et al. |
| 4,795,435 | A | 1/1989 | Steer |
| 4,813,942 | A | 3/1989 | Alvarez |
| 4,820,284 | A | 4/1989 | Hauri |
| 4,826,494 | A | 5/1989 | Richmond et al. |
| 4,828,546 | A | 5/1989 | McNeil et al. |
| 4,921,488 | A | 5/1990 | Maitz et al. |
| 4,936,834 | A | 6/1990 | Beck et al. |
| 4,950,483 | A | 8/1990 | Ksander et al. |
| 4,969,880 | A | 11/1990 | Zamierowski |
| 4,972,829 | A | 11/1990 | Knerr |
| 4,979,944 | A | 12/1990 | Luzsicza |
| 4,994,022 | A | 2/1991 | Steffler et al. |
| 5,055,198 | A | 10/1991 | Shettigar |
| 5,056,510 | A | 10/1991 | Gilman |
| 5,060,642 | A | 10/1991 | Gilman |
| 5,073,172 | A | 12/1991 | Fell |
| 5,100,396 | A | 3/1992 | Zamierowski |
| 5,134,994 | A | 8/1992 | Say |
| 5,149,331 | A | 9/1992 | Ferdman et al. |
| 5,152,757 | A | 10/1992 | Eriksson |
| 5,167,613 | A | 12/1992 | Karami et al. |
| 5,176,663 | A | 1/1993 | Svedman et al. |
| 5,181,905 | A | 1/1993 | Flam |
| 5,215,519 | A | 6/1993 | Shettigar |
| 5,234,419 | A | 8/1993 | Bryant et al. |
| 5,238,732 | A | 8/1993 | Krishnan |
| 5,261,893 | A | 11/1993 | Zarnierowski |
| 5,266,928 | A | 11/1993 | Johnson |
| 5,279,608 | A | 1/1994 | Cherif Cheikh |
| 5,328,614 | A | 7/1994 | Matsumura |
| 5,358,494 | A | 10/1994 | Svedman |
| 5,380,280 | A | 1/1995 | Peterson |
| 5,437,651 | A | 8/1995 | Todd et al. |
| 5,445,604 | A | 8/1995 | Lang |
| 5,489,280 | A | 2/1996 | Russell |
| 5,498,338 | A | 3/1996 | Kruger et al. |
| 5,527,293 | A | 6/1996 | Zamierowski |
| 5,536,233 | A | 7/1996 | Khouri |
| 5,549,584 | A * | 8/1996 | Gross ............... A61M 1/0088 604/313 |
| 5,562,107 | A | 10/1996 | Lavender et al. |
| 5,624,423 | A | 4/1997 | Anjur et al. |
| 5,636,643 | A * | 6/1997 | Argenta ............ A61M 1/0088 128/897 |
| 5,643,189 | A | 7/1997 | Masini |
| 5,645,081 | A | 7/1997 | Argenta et al. |
| 5,662,583 | A | 9/1997 | Khouri |
| 5,676,634 | A | 10/1997 | Khouri |
| 5,678,564 | A * | 10/1997 | Lawrence ............ A61F 5/455 600/573 |
| 5,695,445 | A | 12/1997 | Khouri |
| 5,701,917 | A | 12/1997 | Khouri |
| 5,707,499 | A | 1/1998 | Joshi et al. |
| 5,733,337 | A * | 3/1998 | Carr, Jr. ............... A61L 2/18 435/325 |
| 5,759,570 | A | 6/1998 | Arnold |
| 5,776,098 | A | 7/1998 | Silver et al. |
| 5,785,688 | A | 7/1998 | Joshi et al. |
| 5,817,145 | A | 10/1998 | Augustine et al. |
| 5,830,496 | A | 11/1998 | Freeman |
| 5,833,646 | A | 11/1998 | Masini |
| 5,843,011 | A | 12/1998 | Lucas |
| 5,868,933 | A | 2/1999 | Patrick et al. |
| 5,876,611 | A | 3/1999 | Shettigar |
| 5,964,723 | A | 10/1999 | Augustine |
| 6,010,527 | A | 1/2000 | Augustine et al. |
| 6,013,097 | A | 1/2000 | Augustine et al. |
| 6,071,267 | A | 6/2000 | Zamierowski |
| 6,093,160 | A | 7/2000 | Augustine et al. |
| 6,103,951 | A | 8/2000 | Freeman |
| 6,110,197 | A | 8/2000 | Augustine et al. |
| 6,117,111 | A | 9/2000 | Fleischmann |
| 6,135,116 | A * | 10/2000 | Vogel ............... A61F 13/069 128/898 |
| D434,150 | S | 11/2000 | Tumey et al. |
| 6,142,982 | A * | 11/2000 | Hunt ............... A61M 1/0023 604/313 |
| 6,168,800 | B1 | 1/2001 | Dobos et al. |
| 6,176,307 | B1 | 1/2001 | Danos et al. |
| 6,225,523 | B1 | 5/2001 | Masini |
| 6,248,084 | B1 | 6/2001 | Augustine et al. |
| 6,254,567 | B1 | 7/2001 | Treu et al. |
| 6,255,552 | B1 | 7/2001 | Cummings et al. |
| 6,257,847 | B1 | 7/2001 | Silver et al. |
| 6,261,283 | B1 | 7/2001 | Morgan et al. |
| 6,267,740 | B1 | 7/2001 | Augustine et al. |
| 6,287,521 | B1 | 9/2001 | Quay et al. |
| 6,291,050 | B1 | 9/2001 | Cree et al. |
| 6,293,917 | B1 | 9/2001 | Augustine et al. |
| 6,345,623 | B1 | 2/2002 | Heaton et al. |
| 6,398,767 | B1 * | 6/2002 | Fleischmann ....... A61M 1/0088 604/304 |
| 6,402,724 | B1 | 6/2002 | Smith et al. |
| 6,440,167 | B2 | 8/2002 | Shimizu |
| 6,450,773 | B1 | 9/2002 | Upton |
| 6,458,109 | B1 | 10/2002 | Henley et al. |
| 6,465,708 | B1 | 10/2002 | Augustine |
| 6,468,295 | B2 | 10/2002 | Augustine et al. |
| 6,471,685 | B1 | 10/2002 | Johnson |
| 6,471,982 | B1 | 10/2002 | Lydon et al. |
| 6,481,986 | B1 | 11/2002 | Silver et al. |
| 6,482,491 | B1 | 11/2002 | Samuelsen et al. |
| 6,491,684 | B1 | 12/2002 | Joshi et al. |
| 6,500,112 | B1 | 12/2002 | Khouri |
| 6,547,756 | B1 | 4/2003 | Greter et al. |
| 6,553,998 | B2 | 4/2003 | Heaton et al. |
| 6,580,012 | B1 | 6/2003 | Augustine et al. |
| 6,599,262 | B1 | 7/2003 | Masini |
| 6,626,891 | B2 | 9/2003 | Ohmstede |
| 6,638,270 | B2 | 10/2003 | Johnson |
| 6,648,862 | B2 | 11/2003 | Watson |
| 6,673,028 | B1 | 1/2004 | Argenta et al. |
| 6,676,610 | B2 | 1/2004 | Morton et al. |
| 6,676,631 | B1 | 1/2004 | Greter |

(56) References Cited

U.S. PATENT DOCUMENTS

| | | | |
|---|---|---|---|
| 6,685,681 B2 * | 2/2004 | Lockwood | A61M 1/0058 502/43 |
| 6,695,823 B1 * | 2/2004 | Lina | A61F 13/0203 602/43 |
| 6,695,824 B2 | 2/2004 | Howard et al. | |
| 6,699,213 B1 | 3/2004 | Annis et al. | |
| 6,752,794 B2 | 6/2004 | Lockwood et al. | |
| 6,755,807 B2 * | 6/2004 | Risk, Jr. | A61M 1/0001 604/305 |
| 6,764,462 B2 | 7/2004 | Risk, Jr. et al. | |
| 6,767,334 B1 | 7/2004 | Randolph | |
| 6,775,807 B2 | 8/2004 | Lowther et al. | |
| 6,787,682 B2 | 9/2004 | Gilman | |
| 6,800,074 B2 | 10/2004 | Henley et al. | |
| 6,808,517 B2 | 10/2004 | Greter et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | |
| 6,936,037 B2 | 8/2005 | Bubb | |
| 6,951,553 B2 | 10/2005 | Bubb et al. | |
| 6,960,179 B2 | 11/2005 | Gura | |
| 6,977,323 B1 | 12/2005 | Swenson | |
| 6,979,324 B2 | 12/2005 | Bybordi et al. | |
| 6,987,209 B2 | 1/2006 | Augustine et al. | |
| 6,994,702 B1 | 2/2006 | Johnson | |
| 6,997,897 B1 | 2/2006 | Silver et al. | |
| 7,004,915 B2 | 2/2006 | Boynton et al. | |
| 7,008,400 B2 | 3/2006 | Silver et al. | |
| 7,022,113 B2 | 4/2006 | Lockwood et al. | |
| 7,067,709 B2 | 6/2006 | Murate et al. | |
| 7,070,584 B2 | 7/2006 | Johnson et al. | |
| 7,077,832 B2 | 7/2006 | Fleischmann | |
| 7,087,806 B2 | 8/2006 | Scheinberg et al. | |
| 7,108,683 B2 | 9/2006 | Zamierowski | |
| 7,117,869 B2 | 10/2006 | Heaton et al. | |
| 7,118,545 B2 | 10/2006 | Boyde | |
| 7,122,046 B2 | 10/2006 | Augustine et al. | |
| 7,128,735 B2 | 10/2006 | Weston | |
| 7,141,714 B2 | 11/2006 | Nielsen | |
| 7,195,624 B2 | 3/2007 | Lockwood | |
| 7,214,202 B1 | 5/2007 | Vogel et al. | |
| 7,216,651 B2 | 5/2007 | Argenta et al. | |
| 7,238,850 B2 | 7/2007 | Shimanuki | |
| 7,255,681 B1 | 8/2007 | Silver et al. | |
| 7,273,054 B2 | 9/2007 | Heaton et al. | |
| 7,279,612 B1 | 10/2007 | Heaton et al. | |
| 7,316,672 B1 | 1/2008 | Hunt et al. | |
| 7,335,809 B2 | 2/2008 | Riesinger | |
| 7,338,482 B2 | 3/2008 | Lockwood et al. | |
| 7,361,184 B2 | 4/2008 | Joshi | |
| 7,381,211 B2 | 6/2008 | Zamierowski | |
| 7,381,859 B2 | 6/2008 | Hunt et al. | |
| 7,438,705 B2 | 10/2008 | Karpowicz et al. | |
| 7,470,830 B2 | 12/2008 | Sigurjonsson et al. | |
| 7,485,112 B2 | 2/2009 | Karpowicz et al. | |
| 7,494,482 B2 | 2/2009 | Orgill et al. | |
| 7,503,910 B2 | 3/2009 | Adahz--In | |
| 7,507,870 B2 | 3/2009 | Nielsen et al. | |
| 7,524,286 B2 | 4/2009 | Johnson | |
| 7,524,315 B2 | 4/2009 | Blott et al. | |
| 7,534,240 B1 | 5/2009 | Johnson | |
| 7,534,927 B2 | 5/2009 | Lockwood | |
| 7,569,742 B2 | 8/2009 | Haggstrom et al. | |
| 7,601,129 B2 | 10/2009 | Aali | |
| 7,605,298 B2 | 10/2009 | Bechert et al. | |
| 7,611,500 B1 | 11/2009 | Lina et al. | |
| 7,612,247 B2 | 11/2009 | Oyaski | |
| 7,615,036 B2 | 11/2009 | Joshi et al. | |
| 7,622,629 B2 | 11/2009 | Aail | |
| 7,625,362 B2 | 12/2009 | Boehringer | |
| 7,645,253 B2 | 1/2010 | Gura et al. | |
| 7,645,269 B2 | 1/2010 | Zamierowski | |
| 7,670,323 B2 | 3/2010 | Hunt et al. | |
| 7,678,090 B2 | 3/2010 | Risk, Jr. et al. | |
| 7,699,823 B2 | 4/2010 | Haggstrom et al. | |
| 7,699,830 B2 | 4/2010 | Martin | |
| 7,700,819 B2 | 4/2010 | Ambrosio et al. | |
| 7,708,724 B2 | 5/2010 | Weston | |
| 7,717,313 B2 | 5/2010 | Criscuolo et al. | |
| 7,722,582 B2 | 5/2010 | Lina et al. | |
| 7,731,702 B2 | 6/2010 | Bybordi et al. | |
| 7,745,681 B1 | 6/2010 | Ferguson | |
| 7,749,531 B2 | 7/2010 | Booher | |
| 7,753,894 B2 | 7/2010 | Blott et al. | |
| 7,754,936 B2 | 7/2010 | Heaton et al. | |
| 7,758,514 B2 | 7/2010 | Grigoryants et al. | |
| 7,758,554 B2 | 7/2010 | Lina et al. | |
| 7,759,537 B2 | 7/2010 | Bishop et al. | |
| 7,759,538 B2 | 7/2010 | Fleischmann | |
| 7,759,539 B2 | 7/2010 | Shaw et al. | |
| 7,763,000 B2 | 7/2010 | Risk, Jr. et al. | |
| 7,775,998 B2 | 8/2010 | Riesinger | |
| 7,776,028 B2 | 8/2010 | Miller et al. | |
| 7,779,625 B2 | 8/2010 | Joshi et al. | |
| 7,790,945 B1 | 9/2010 | Watson, Jr. | |
| 7,790,946 B2 | 9/2010 | Mulligan | |
| 7,794,438 B2 | 9/2010 | Henley et al. | |
| 7,794,450 B2 | 9/2010 | Blott et al. | |
| 7,803,980 B2 | 9/2010 | Griffiths et al. | |
| 7,811,269 B2 | 10/2010 | Boynton et al. | |
| 7,812,212 B2 | 10/2010 | Propp et al. | |
| 7,815,616 B2 | 10/2010 | Boehringer et al. | |
| 7,816,577 B2 | 10/2010 | Aali | |
| 7,825,289 B2 | 11/2010 | Vess | |
| 7,828,782 B2 | 11/2010 | Suzuki | |
| 7,838,716 B2 | 11/2010 | de Luis et al. | |
| 7,838,717 B2 | 11/2010 | Haggstrom et al. | |
| 7,846,141 B2 | 12/2010 | Weston | |
| 7,857,806 B2 | 12/2010 | Karpowicz et al. | |
| 7,858,838 B2 | 12/2010 | Holm et al. | |
| 7,862,339 B2 | 1/2011 | Mulligan | |
| 7,867,206 B2 | 1/2011 | Lockwood et al. | |
| 7,880,050 B2 | 2/2011 | Robinson et al. | |
| 7,883,494 B2 | 2/2011 | Martin | |
| 7,884,258 B2 | 2/2011 | Boehringer et al. | |
| 7,886,746 B2 | 2/2011 | Heaton et al. | |
| 7,896,823 B2 | 3/2011 | Mangrum et al. | |
| 7,896,856 B2 | 3/2011 | Petrosenko et al. | |
| 7,909,805 B2 | 3/2011 | Weston | |
| 7,910,791 B2 | 3/2011 | Coffey | |
| 7,922,703 B2 | 4/2011 | Riesinger | |
| 7,927,318 B2 | 4/2011 | Risk, Jr. et al. | |
| 7,931,630 B2 | 4/2011 | Nishtala et al. | |
| 7,951,100 B2 | 5/2011 | Hunt et al. | |
| 7,951,124 B2 | 5/2011 | Boehringer et al. | |
| 7,959,624 B2 | 6/2011 | Riesinger | |
| 7,964,766 B2 | 6/2011 | Blott et al. | |
| 7,976,519 B2 | 7/2011 | Bubb et al. | |
| D642,594 S | 8/2011 | Mattson et al. | |
| 7,988,680 B2 | 8/2011 | Lockwood et al. | |
| 7,998,125 B2 | 8/2011 | Weston | |
| 8,007,257 B2 | 8/2011 | Heaton et al. | |
| 8,012,169 B2 | 9/2011 | Joshi | |
| 8,021,348 B2 | 9/2011 | Risk, Jr. et al. | |
| 8,022,266 B2 | 9/2011 | Boehringer et al. | |
| 8,025,650 B2 | 9/2011 | Anderson et al. | |
| 8,034,037 B2 | 10/2011 | Adams et al. | |
| 8,034,038 B2 | 10/2011 | Biggie et al. | |
| 8,062,272 B2 | 11/2011 | Weston | |
| 8,062,273 B2 | 11/2011 | Weston | |
| 8,062,331 B2 | 11/2011 | Zamierowski | |
| 8,080,702 B2 | 12/2011 | Blott et al. | |
| 8,084,663 B2 | 12/2011 | Watson, Jr. | |
| 8,092,441 B2 | 1/2012 | Sugito | |
| 8,100,887 B2 | 1/2012 | Weston et al. | |
| 8,105,295 B2 | 1/2012 | Blott et al. | |
| 8,118,794 B2 | 2/2012 | Weston | |
| 8,128,615 B2 | 3/2012 | Blott et al. | |
| 8,133,211 B2 | 3/2012 | Cavanaugh, Ii et al. | |
| 8,147,468 B2 | 4/2012 | Barta et al. | |
| 8,152,785 B2 | 4/2012 | Vitaris | |
| 8,158,844 B2 | 4/2012 | McNeil | |
| 8,162,907 B2 | 4/2012 | Heagle | |

(56) References Cited

U.S. PATENT DOCUMENTS

| | | |
|---|---|---|
| 8,162,909 B2 | 4/2012 | Blott et al. |
| 8,168,848 B2 | 5/2012 | Lockwood et al. |
| 8,188,331 B2 | 5/2012 | Barta et al. |
| 8,202,261 B2 | 6/2012 | Kazala, Jr. et al. |
| 8,207,392 B2 | 6/2012 | Haggstrom et al. |
| 8,211,071 B2 | 7/2012 | Mormino et al. |
| 8,215,929 B2 | 7/2012 | Shen et al. |
| 8,235,955 B2 | 8/2012 | Blott et al. |
| 8,241,261 B2 | 8/2012 | Randolph et al. |
| 8,251,979 B2 | 8/2012 | Malhi |
| 8,257,326 B2 | 9/2012 | Vitaris |
| 8,257,327 B2 | 9/2012 | Blott et al. |
| 8,257,328 B2 | 9/2012 | Augustine et al. |
| 8,267,908 B2 | 9/2012 | Coulthard |
| 8,282,611 B2 | 10/2012 | Weston |
| 8,294,586 B2 | 10/2012 | Pidgeon et al. |
| 8,303,552 B2 | 11/2012 | Weston |
| 8,308,714 B2 | 11/2012 | Weston et al. |
| 8,317,774 B2 | 11/2012 | Adahan |
| 8,323,264 B2 | 12/2012 | Weston et al. |
| 8,348,910 B2 | 1/2013 | Blott et al. |
| 8,372,049 B2 | 2/2013 | Jaeb et al. |
| 8,372,050 B2 | 2/2013 | Jaeb et al. |
| 8,376,972 B2 | 2/2013 | Fleischmann |
| 8,382,731 B2 | 2/2013 | Johannison |
| 8,398,614 B2 | 3/2013 | Blott et al. |
| 8,399,730 B2 | 3/2013 | Kazala et al. |
| 8,404,921 B2 | 3/2013 | Lee et al. |
| D679,819 S | 4/2013 | Peron |
| D679,820 S | 4/2013 | Peron |
| 8,425,478 B2 | 4/2013 | Olson |
| 8,444,612 B2 | 5/2013 | Patel et al. |
| 8,449,509 B2 | 5/2013 | Weston |
| 8,460,225 B2 | 6/2013 | Wickstrom |
| 8,460,255 B2 | 6/2013 | Joshi et al. |
| 8,494,349 B2 | 7/2013 | Gordon |
| 8,506,554 B2 | 8/2013 | Adahan |
| 8,513,481 B2 | 8/2013 | Gergeley et al. |
| 8,535,283 B2 | 9/2013 | Heaton et al. |
| 8,545,464 B2 | 10/2013 | Weston |
| 8,545,466 B2 | 10/2013 | Andresen et al. |
| 8,556,871 B2 | 10/2013 | Mormino et al. |
| 8,569,566 B2 | 10/2013 | Blott et al. |
| 8,628,505 B2 | 1/2014 | Weston |
| 8,641,691 B2 | 2/2014 | Fink |
| 8,663,198 B2 | 3/2014 | Buan et al. |
| 8,679,079 B2 | 3/2014 | Heaton et al. |
| 8,708,998 B2 | 4/2014 | Weston et al. |
| 8,715,256 B2 | 5/2014 | Greener |
| 8,721,606 B2 | 5/2014 | Simmons |
| 8,728,044 B2 | 5/2014 | Coulthard et al. |
| 8,764,732 B2 | 7/2014 | Hartwell |
| 8,784,393 B2 | 7/2014 | Weston et al. |
| 8,795,243 B2 | 8/2014 | Weston |
| 8,795,244 B2 | 8/2014 | Randolph et al. |
| 8,795,800 B2 | 8/2014 | Evans |
| 8,808,274 B2 | 8/2014 | Hartwell |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,843,327 B2 | 9/2014 | Vernon-Harcourt et al. |
| 8,864,748 B2 | 10/2014 | Coulthard et al. |
| 8,905,985 B2 | 12/2014 | Allen et al. |
| 8,911,681 B2 | 12/2014 | Song et al. |
| 8,926,592 B2 | 1/2015 | Blott et al. |
| 8,956,336 B2 | 2/2015 | Haggstrom et al. |
| 9,012,714 B2 | 4/2015 | Fleischmann |
| 9,033,942 B2 | 5/2015 | Vess |
| 9,044,579 B2 | 6/2015 | Blott et al. |
| 9,061,095 B2 | 6/2015 | Adie et al. |
| 9,127,665 B2 | 9/2015 | Locke et al. |
| 9,168,180 B2 | 10/2015 | Ha et al. |
| 9,168,330 B2 | 10/2015 | Joshi et al. |
| 9,199,012 B2 | 12/2015 | Vitaris et al. |
| 9,220,822 B2 | 12/2015 | Hartwell et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,414,968 B2 | 8/2016 | Heagle |
| 9,421,309 B2 | 8/2016 | Robinson et al. |
| 9,446,178 B2 | 9/2016 | Blott et al. |
| 9,452,248 B2 | 9/2016 | Blott et al. |
| 2001/0029956 A1* | 10/2001 | Argenta ............... A61M 1/0088 128/897 |
| 2001/0031911 A1 | 10/2001 | Khouri |
| 2001/0034499 A1 | 10/2001 | Sessions et al. |
| 2001/0043943 A1 | 11/2001 | Coffey |
| 2002/0002209 A1 | 1/2002 | Mork |
| 2002/0026133 A1 | 2/2002 | Augustine et al. |
| 2002/0068913 A1 | 6/2002 | Fleischmann |
| 2002/0082567 A1 | 6/2002 | Lockwood et al. |
| 2002/0143286 A1 | 10/2002 | Tumey |
| 2002/0161317 A1 | 10/2002 | Risk et al. |
| 2002/0183702 A1 | 12/2002 | Henley et al. |
| 2003/0014025 A1 | 1/2003 | Allen et al. |
| 2003/0021775 A1 | 1/2003 | Freeman |
| 2003/0023286 A1 | 1/2003 | Augustine et al. |
| 2003/0045825 A1 | 3/2003 | Etheredge, III |
| 2003/0069529 A1 | 4/2003 | Augustine et al. |
| 2003/0069536 A1 | 4/2003 | Greter et al. |
| 2003/0069563 A1 | 4/2003 | Johnson |
| 2003/0125649 A1 | 7/2003 | McIntosh et al. |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0188754 A1 | 10/2003 | Heaton et al. |
| 2003/0212357 A1 | 11/2003 | Pace |
| 2003/0212431 A1 | 11/2003 | Brady et al. |
| 2003/0219469 A1 | 11/2003 | Johnson et al. |
| 2003/0225347 A1 | 12/2003 | Argenta et al. |
| 2004/0019342 A1 | 1/2004 | Nagasuna et al. |
| 2004/0024351 A1 | 2/2004 | Greter et al. |
| 2004/0039391 A1 | 2/2004 | Argenta et al. |
| 2004/0039415 A1 | 2/2004 | Zamierowski |
| 2004/0054338 A1 | 3/2004 | Bybordi et al. |
| 2004/0064111 A1 | 4/2004 | Lockwood et al. |
| 2004/0064132 A1 | 4/2004 | Boehringer et al. |
| 2004/0073151 A1* | 4/2004 | Weston ............... A61F 15/008 602/41 |
| 2004/0122434 A1 | 6/2004 | Argenta et al. |
| 2004/0127862 A1 | 7/2004 | Bubb et al. |
| 2004/0127863 A1 | 7/2004 | Bubb et al. |
| 2004/0167482 A1 | 8/2004 | Watson |
| 2004/0171976 A1 | 9/2004 | Johson |
| 2004/0241214 A1 | 12/2004 | Kirkwood et al. |
| 2004/0249353 A1 | 12/2004 | Risk, Jr. et al. |
| 2005/0020955 A1 | 1/2005 | Sanders et al. |
| 2005/0058694 A1* | 3/2005 | Nielsen ............... A61L 15/28 424/445 |
| 2005/0070835 A1* | 3/2005 | Joshi ............... A61M 1/0066 602/41 |
| 2005/0085768 A1 | 4/2005 | Greter et al. |
| 2005/0090787 A1 | 4/2005 | Risk et al. |
| 2005/0131327 A1 | 6/2005 | Lockwood et al. |
| 2005/0148913 A1* | 7/2005 | Weston ............... A61M 1/0088 602/2 |
| 2005/0165350 A1 | 7/2005 | Greter et al. |
| 2005/0222544 A1* | 10/2005 | Weston ............... A61M 1/0001 604/313 |
| 2005/0228329 A1 | 10/2005 | Boehringer et al. |
| 2005/0245850 A1 | 11/2005 | Freyre et al. |
| 2005/0261642 A1* | 11/2005 | Weston ............... A61M 1/0088 604/313 |
| 2005/0283105 A1 | 12/2005 | Heaton et al. |
| 2006/0009744 A1 | 1/2006 | Edrman et al. |
| 2006/0029650 A1* | 2/2006 | Coffey ............... A61F 13/02 424/443 |
| 2006/0069365 A1 | 3/2006 | Sperl et al. |
| 2006/0070458 A1 | 4/2006 | Jones et al. |
| 2006/0100586 A1 | 5/2006 | Karpowicz |
| 2006/0149170 A1 | 7/2006 | Boynton et al. |

(56) References Cited

U.S. PATENT DOCUMENTS

| | | |
|---|---|---|
| 2006/0155260 A1* | 7/2006 | Blott .................. A61M 1/0058 604/543 |
| 2006/0282028 A1 | 12/2006 | Howard et al. |
| 2007/0005028 A1 | 1/2007 | Risk et al. |
| 2007/0021697 A1 | 1/2007 | Ginther et al. |
| 2007/0032762 A1 | 2/2007 | Vogel |
| 2007/0032778 A1 | 2/2007 | Heaton et al. |
| 2007/0038172 A1 | 2/2007 | Zamierowski |
| 2007/0055209 A1 | 3/2007 | Patel et al. |
| 2007/0167884 A1 | 7/2007 | Mangrum et al. |
| 2007/0179460 A1 | 8/2007 | Adahan |
| 2007/0185463 A1 | 8/2007 | Mulligan |
| 2007/0219513 A1 | 9/2007 | Lina et al. |
| 2007/0219532 A1 | 9/2007 | Karpowicz et al. |
| 2007/0225663 A1 | 9/2007 | Watt et al. |
| 2007/0260207 A1 | 11/2007 | Ugander et al. |
| 2008/0009812 A1 | 1/2008 | Riesinger |
| 2008/0033352 A1 | 2/2008 | Annis et al. |
| 2008/0039761 A1 | 2/2008 | Heaton et al. |
| 2008/0045887 A1 | 2/2008 | Larsson et al. |
| 2008/0132821 A1 | 6/2008 | Propp et al. |
| 2008/0188820 A1 | 8/2008 | Joshi |
| 2008/0200905 A1 | 8/2008 | Heaton |
| 2008/0223378 A1 | 9/2008 | Henderson et al. |
| 2008/0234641 A1 | 9/2008 | Locke et al. |
| 2008/0294147 A1 | 11/2008 | Radl et al. |
| 2008/0306407 A1 | 12/2008 | Taylor |
| 2008/0306456 A1 | 12/2008 | Riesinger |
| 2008/0312572 A1 | 12/2008 | Riesinger |
| 2008/0312613 A1 | 12/2008 | Heaton et al. |
| 2009/0005746 A1 | 1/2009 | Nielsen et al. |
| 2009/0036873 A1 | 2/2009 | Nielsen et al. |
| 2009/0054855 A1 | 2/2009 | Blott et al. |
| 2009/0054856 A1 | 2/2009 | Mormino et al. |
| 2009/0082740 A1 | 3/2009 | Lockwood et al. |
| 2009/0093779 A1 | 4/2009 | Riesinger |
| 2009/0125004 A1 | 5/2009 | Shen et al. |
| 2009/0131888 A1 | 5/2009 | Joshi |
| 2009/0131892 A1 | 5/2009 | Karpowicz et al. |
| 2009/0137973 A1 | 5/2009 | Karpowicz et al. |
| 2009/0157024 A1 | 6/2009 | Song |
| 2009/0192467 A1 | 7/2009 | Hansen et al. |
| 2009/0198201 A1 | 8/2009 | Adahan |
| 2009/0204085 A1 | 8/2009 | Biggie et al. |
| 2009/0216170 A1 | 8/2009 | Robinson et al. |
| 2009/0216204 A1 | 8/2009 | Bhavaraju et al. |
| 2009/0221977 A1 | 9/2009 | Blott et al. |
| 2009/0234306 A1 | 9/2009 | Vitaris |
| 2009/0240218 A1 | 9/2009 | Braga et al. |
| 2009/0254053 A1 | 10/2009 | Svensby et al. |
| 2009/0254066 A1 | 10/2009 | Heaton |
| 2009/0259203 A1 | 10/2009 | Hu et al. |
| 2009/0264807 A1 | 10/2009 | Haggstrom et al. |
| 2009/0270820 A1 | 10/2009 | Johnson |
| 2009/0275922 A1 | 11/2009 | Coulthard et al. |
| 2009/0287129 A1 | 11/2009 | Boehringer et al. |
| 2009/0293887 A1 | 12/2009 | Wilkes et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299306 A1 | 12/2009 | Buan |
| 2009/0312723 A1 | 12/2009 | Blott et al. |
| 2010/0004611 A1 | 1/2010 | Aali |
| 2010/0016767 A1 | 1/2010 | Jones et al. |
| 2010/0022972 A1 | 1/2010 | Lina et al. |
| 2010/0030170 A1 | 2/2010 | Keller et al. |
| 2010/0030171 A1 | 2/2010 | Canada et al. |
| 2010/0030178 A1 | 2/2010 | MacMeccan et al. |
| 2010/0036334 A1 | 2/2010 | Heagle et al. |
| 2010/0036367 A1 | 2/2010 | Krohn |
| 2010/0069858 A1 | 3/2010 | Olson |
| 2010/0069863 A1 | 3/2010 | Olson |
| 2010/0106112 A1 | 4/2010 | Vogel |
| 2010/0106117 A1 | 4/2010 | Lockwood et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0145289 A1 | 6/2010 | Line et al. |
| 2010/0159192 A1 | 6/2010 | Cotton |
| 2010/0160878 A1 | 6/2010 | Hunt et al. |
| 2010/0174251 A1* | 7/2010 | Weston ............... A61M 1/0088 604/320 |
| 2010/0210986 A1 | 8/2010 | Sanders |
| 2010/0249733 A9 | 9/2010 | Blott et al. |
| 2010/0262090 A1 | 10/2010 | Riesinger |
| 2010/0262091 A1 | 10/2010 | Larsson |
| 2010/0280468 A1 | 11/2010 | Haggstrom et al. |
| 2010/0305490 A1 | 12/2010 | Coulthard et al. |
| 2010/0318052 A1* | 12/2010 | Ha .......................... A61F 13/02 604/385.01 |
| 2011/0004172 A1 | 1/2011 | Eckstein et al. |
| 2011/0004173 A1 | 1/2011 | Hu et al. |
| 2011/0022013 A1 | 1/2011 | Boynton et al. |
| 2011/0028919 A1 | 2/2011 | Johnnison et al. |
| 2011/0028920 A1 | 2/2011 | Johannison |
| 2011/0028921 A1 | 2/2011 | Hartwell et al. |
| 2011/0034869 A1 | 2/2011 | Greter et al. |
| 2011/0034888 A1 | 2/2011 | Aali |
| 2011/0034894 A1 | 2/2011 | Riesinger |
| 2011/0054423 A1 | 3/2011 | Blott et al. |
| 2011/0092958 A1 | 4/2011 | Jacobs |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1* | 5/2011 | Weston ................. A61F 5/048 604/319 |
| 2011/0125066 A1 | 5/2011 | Robinson et al. |
| 2011/0130712 A1 | 6/2011 | Topaz |
| 2011/0172617 A1 | 7/2011 | Riesinger |
| 2011/0270201 A1 | 11/2011 | Bubb et al. |
| 2011/0270202 A1 | 11/2011 | Boehringer et al. |
| 2011/0295220 A1 | 12/2011 | Heaton et al. |
| 2011/0313373 A1 | 12/2011 | Riesinger |
| 2011/0313374 A1 | 12/2011 | Lockwood et al. |
| 2012/0053538 A1 | 3/2012 | Blott et al. |
| 2012/0109085 A1 | 5/2012 | McNeil |
| 2012/0130332 A1 | 5/2012 | Cotton et al. |
| 2013/0066285 A1 | 3/2013 | Locke et al. |
| 2013/0090615 A1 | 4/2013 | Jaeb et al. |
| 2013/0102979 A1 | 4/2013 | Coulthard et al. |
| 2013/0138054 A1 | 5/2013 | Fleischmann |
| 2013/0144230 A1 | 6/2013 | Wu et al. |
| 2013/0150814 A1 | 6/2013 | Buan |
| 2013/0165878 A1 | 6/2013 | Heagle |
| 2013/0274688 A1 | 10/2013 | Weston |
| 2013/0331822 A1 | 12/2013 | Patel et al. |
| 2013/0338614 A1 | 12/2013 | Heaton et al. |
| 2014/0114268 A1 | 4/2014 | Auguste et al. |
| 2014/0155849 A1 | 6/2014 | Heaton et al. |
| 2014/0228791 A1 | 8/2014 | Hartwell |
| 2015/0032035 A1 | 1/2015 | Banwell et al. |
| 2015/0065965 A1 | 3/2015 | Haggstrom et al. |
| 2015/0174304 A1 | 6/2015 | Askem et al. |
| 2015/0190286 A1 | 7/2015 | Allen et al. |
| 2015/0209492 A1 | 7/2015 | Blott et al. |
| 2015/0216733 A1 | 8/2015 | Allen et al. |
| 2015/0308994 A1 | 10/2015 | Hammond et al. |
| 2016/0051737 A1 | 2/2016 | Joshi et al. |
| 2016/0081859 A1 | 3/2016 | Hartwell |
| 2016/0317357 A1 | 11/2016 | Vitaris et al. |
| 2017/0095598 A1 | 4/2017 | Joshi et al. |
| 2017/0128642 A1 | 5/2017 | Buan |
| 2017/0181896 A1 | 6/2017 | Hartwell |
| 2017/0181897 A1 | 6/2017 | Hartwell |

FOREIGN PATENT DOCUMENTS

| | | |
|---|---|---|
| CA | 2 390 513 | 5/2001 |
| CA | 2 121 688 | 7/2001 |
| CA | 2 408 305 | 11/2001 |
| CA | 2 458 285 | 3/2003 |
| CA | 2 157 772 | 9/2003 |
| CN | 2186074 | 12/1994 |
| DE | 847475 | 8/1952 |

(56) References Cited

FOREIGN PATENT DOCUMENTS

| | | |
|---|---|---|
| DE | 2 809 828 | 9/1978 |
| DE | 3 032 092 | 8/1980 |
| DE | 3 137 839 | 3/1983 |
| DE | 34 43 101 | 5/1986 |
| DE | 3 935 818 | 5/1991 |
| DE | 4 012 232 | 10/1991 |
| DE | 90 17 289 | 6/1992 |
| DE | 198 44 355 | 4/2000 |
| DE | 20 2004 017 052 | 7/2005 |
| EP | 0 020 662 | 7/1984 |
| EP | 0 257 916 | 3/1988 |
| EP | 0 340 018 | 11/1989 |
| EP | 0 355 186 | 2/1990 |
| EP | 0 541 251 | 5/1993 |
| EP | 0 619 105 | 10/1994 |
| EP | 0 777 504 | 10/1998 |
| EP | 0 782 421 | 7/1999 |
| EP | 1 013 290 | 6/2000 |
| EP | 1 411 874 | 7/2001 |
| EP | 1 897 569 | 8/2002 |
| EP | 0 708 620 | 5/2003 |
| EP | 1 088 569 | 8/2003 |
| EP | 1 452 156 | 9/2004 |
| EP | 1 440 667 | 3/2006 |
| EP | 1 284 777 | 4/2006 |
| EP | 1 726 276 | 11/2006 |
| EP | 1 923 077 | 11/2006 |
| EP | 1 171 065 | 3/2007 |
| EP | 1 880 840 | 1/2008 |
| EP | 1 476 217 | 3/2008 |
| EP | 1 985 270 | 10/2008 |
| EP | 1 121 163 | 11/2008 |
| EP | 2 185 206 | 1/2009 |
| EP | 2 178 573 | 2/2009 |
| EP | 2 079 507 | 7/2009 |
| EP | 2 098 257 | 9/2009 |
| EP | 1 985 270 | 12/2009 |
| EP | 2 161 011 | 3/2010 |
| EP | 2 326 295 | 3/2010 |
| EP | 1 718257 | 8/2010 |
| EP | 2 335 749 | 6/2011 |
| EP | 2 349 155 | 8/2011 |
| EP | 1 263 366 | 9/2011 |
| EP | 2 420 214 | 2/2012 |
| EP | 2 021 046 | 3/2012 |
| EP | 2 462 908 | 6/2012 |
| EP | 2 711 034 | 3/2014 |
| EP | 2 305 325 | 4/2014 |
| EP | 2 345 437 | 4/2014 |
| EP | 2 687 245 | 9/2014 |
| EP | 2 648 668 | 1/2015 |
| FR | 1163907 | 10/1958 |
| GB | 114754 | 4/1918 |
| GB | 236350 | 7/1925 |
| GB | 641061 | 8/1950 |
| GB | 1224009 | 3/1971 |
| GB | 1255395 | 12/1971 |
| GB | 1400124 | 7/1975 |
| GB | 1549756 | 8/1979 |
| GB | 2099306 | 12/1982 |
| GB | 2195255 | 4/1988 |
| GB | 2307180 | 5/1997 |
| GB | 2378392 | 2/2003 |
| GB | 2415908 | 1/2006 |
| GB | 2 435 422 | 8/2007 |
| JP | 59-86824 | 6/1984 |
| JP | 59-87824 | 6/1984 |
| JP | S61-80018 | 5/1986 |
| JP | 2003-165843 | 6/2003 |
| JP | 2005-334188 | 12/2005 |
| SU | 1251912 A1 | 4/1983 |
| WO | WO 1983/00742 | 3/1983 |
| WO | WO 1984/01904 | 5/1984 |
| WO | WO 1990/11795 | 10/1990 |
| WO | WO 1991/00718 | 1/1991 |
| WO | WO 1992/20299 | 11/1992 |
| WO | WO 1994/20041 | 9/1994 |
| WO | WO 1994/23677 | 10/1994 |
| WO | WO 1995/04511 | 2/1995 |
| WO | WO 1995/14451 | 6/1995 |
| WO | WO 1995/29959 | 11/1995 |
| WO | WO 1996/05873 | 2/1996 |
| WO | WO 1996/21410 | 7/1996 |
| WO | WO 1997/11658 | 4/1997 |
| WO | WO 1999/01173 | 1/1999 |
| WO | WO 1999/39671 | 8/1999 |
| WO | WO 2000/07653 | 2/2000 |
| WO | WO 2000/42957 | 7/2000 |
| WO | WO 2000/50143 | 8/2000 |
| WO | WO 2000/59424 | 10/2000 |
| WO | WO 2001/19430 | 3/2001 |
| WO | WO 2001/34223 | 5/2001 |
| WO | WO 2001/37922 A2 | 5/2001 |
| WO | WO 2001/37922 A3 | 5/2001 |
| WO | WO 2001/85248 | 11/2001 |
| WO | WO 2001/93793 | 12/2001 |
| WO | WO 2002/17840 | 3/2002 |
| WO | WO 2002/26180 | 4/2002 |
| WO | WO 2002/38096 | 5/2002 |
| WO | WO 2002/076379 | 10/2002 |
| WO | WO 2002/083046 | 10/2002 |
| WO | WO 2002/092783 | 11/2002 |
| WO | WO 2003/045492 | 6/2003 |
| WO | WO 2003/057307 | 7/2003 |
| WO | WO 2003/092620 | 11/2003 |
| WO | WO 2004/024300 | 3/2004 |
| WO | WO 2004/037334 | 5/2004 |
| WO | WO 2004/073566 | 9/2004 |
| WO | WO 2005/009488 | 2/2005 |
| WO | WO 2005/016179 | 2/2005 |
| WO | WO 2005/025447 | 3/2005 |
| WO | WO 2005/025666 | 3/2005 |
| WO | WO 2005/046761 | 5/2005 |
| WO | WO 2005/051461 | 6/2005 |
| WO | WO 2005/070480 | 8/2005 |
| WO | WO 2005/079718 | 9/2005 |
| WO | WO 2005/082435 | 9/2005 |
| WO | WO 2005/105180 | 11/2005 |
| WO | WO 2005/123170 | 12/2005 |
| WO | WO 2006/048246 | 5/2006 |
| WO | WO 2006/052745 | 5/2006 |
| WO | WO 2006/052839 | 5/2006 |
| WO | WO 2006/056294 | 6/2006 |
| WO | WO 2006/081403 | 8/2006 |
| WO | WO 2006/116992 | 11/2006 |
| WO | WO 2007/002835 | 1/2007 |
| WO | WO 2007/013064 | 2/2007 |
| WO | WO 2007/019038 | 2/2007 |
| WO | WO 2007/024230 | 3/2007 |
| WO | WO 2007/030598 | 3/2007 |
| WO | WO 2007/030599 | 3/2007 |
| WO | WO 2007/030601 | 3/2007 |
| WO | WO 2007/084792 | 7/2007 |
| WO | WO 2007/085396 | 8/2007 |
| WO | WO 2007/092405 | 8/2007 |
| WO | WO 2007/106592 | 9/2007 |
| WO | WO 2007/133618 | 11/2007 |
| WO | WO 2008/013896 | 1/2008 |
| WO | WO 2008/027449 | 3/2008 |
| WO | WO 2008/040020 | 4/2008 |
| WO | WO 2008/041926 | 4/2008 |
| WO | WO 2008/049277 | 5/2008 |
| WO | WO 2008/100437 | 8/2008 |
| WO | WO 2008/100440 | 8/2008 |
| WO | WO 2008/112304 | 9/2008 |
| WO | WO 2008/131985 | 11/2008 |
| WO | WO 2009/019227 | 2/2009 |
| WO | WO 2009/019229 | 2/2009 |
| WO | WO 2009/146441 | 3/2009 |
| WO | WO 2009/047524 | 4/2009 |
| WO | WO 2009/062327 | 5/2009 |
| WO | WO 2009/066104 | 5/2009 |
| WO | WO 2009/066105 | 5/2009 |
| WO | WO 2009/066106 | 5/2009 |

(56) References Cited

FOREIGN PATENT DOCUMENTS

| | | |
|---|---|---|
| WO | WO 2009/089390 | 7/2009 |
| WO | WO 2009/103031 | 8/2009 |
| WO | WO 2009/111657 | 9/2009 |
| WO | WO 2009/117635 | 9/2009 |
| WO | WO 2009/122989 | 10/2009 |
| WO | WO 2009/124100 | 10/2009 |
| WO | WO 2009/126833 | 10/2009 |
| WO | WO 2009/146441 | 12/2009 |
| WO | WO 2009/151380 | 12/2009 |
| WO | WO 2009/156709 | 12/2009 |
| WO | WO 2009/158124 | 12/2009 |
| WO | WO 2009/158128 | 12/2009 |
| WO | WO 2009/158130 | 12/2009 |
| WO | WO 2010/026251 | 3/2010 |
| WO | WO 2010/042240 | 4/2010 |
| WO | WO 2010/051418 | 5/2010 |
| WO | WO 2010/059849 | 5/2010 |
| WO | WO 2010/072309 | 7/2010 |
| WO | WO 2010/072395 | 7/2010 |
| WO | WO 2010/082872 | 7/2010 |
| WO | WO 2010/089448 | 8/2010 |
| WO | WO 2010/120776 | 10/2010 |
| WO | WO 2010/139926 | 12/2010 |
| WO | WO 2010/141271 | 12/2010 |
| WO | WO 2010/142959 | 12/2010 |
| WO | WO 2010/147592 | 12/2010 |
| WO | WO 2011/019476 | 2/2011 |
| WO | WO 2011/023275 | 3/2011 |
| WO | WO 2011/023650 | 3/2011 |
| WO | WO 2011/128651 | 10/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2012/009370 | 1/2012 |
| WO | WO 2012/022484 | 2/2012 |
| WO | WO 2012/074512 | 6/2012 |
| WO | WO 2012/131237 | 10/2012 |
| WO | WO 2012/140378 | 10/2012 |
| WO | WO 2012/143665 | 10/2012 |
| WO | WO 2012/146656 | 11/2012 |
| WO | WO 2012/150235 | 11/2012 |
| WO | WO 2012/151359 | 11/2012 |
| WO | WO 2013/010907 | 1/2013 |
| WO | WO 2013/083800 | 6/2013 |
| WO | WO 2013/090810 | 6/2013 |
| WO | WO 2013/149078 | 10/2013 |
| WO | WO 2014/008348 | 1/2014 |
| WO | WO 2014/016759 | 1/2014 |
| WO | WO 2014/108476 | 7/2014 |
| WO | WO 2014/113253 | 7/2014 |
| WO | WO 2015/022334 | 2/2015 |
| WO | WO 2015/022340 | 2/2015 |

OTHER PUBLICATIONS

US 6,306,115, 10/2001, Kelly et al. (withdrawn)
U.S. Appl. No. 13/212,039, Wound Cleansing Apparatus In-Situ, filed Aug. 17, 2011.
U.S. Appl. No. 14/575,968, Wound Cleansing Apparatus In-Situ, filed Dec. 18, 2014.
U.S. Appl. No. 14/254,807, Vacuum Assisted Wound Dressing, filed Apr. 16, 2014.
U.S. Appl. No. 14/259,026, Wound Dressing, Apr. 22, 2014.
U.S. Appl. No. 14/276,983, Wound Dressing, filed May 13, 2014.
U.S. Appl. No. 13/092,042, Wound Dressing and Method of Use, filed Apr. 21, 2011.
U.S. Appl. No. 13/287,897, Reduced Pressure Therapy Apparatuses and Methods of Using Same, filed Nov. 2, 2011.
U.S. Appl. No. 14/142,635, Reduced Pressure Treatment System, filed Dec. 27, 2013.
U.S. Appl. No. 12/941,390, Reduced Pressure Wound Treatment System, filed Nov. 8, 2010.
U.S. Appl. No. 13/859,670, Reduced Presure Treatment System, filed Apr. 9, 2013.
U.S. Appl. No. 13/902,446, Flexible Reduced Treatment Appliance, filed May 24, 2013.
U.S. Appl. No. 13/912,716, Device and Method for Wound Therapy, filed Jun. 7, 2013.
U.S. Appl. No. 13/760,610, Negative Pressure Wound Therapy Device, filed Feb. 6, 2013.
Achterberg, V., Ph.D., Hydroactive dressings and serum proteins: an in vitro study, Journal of Wound Care, February, vol. 5, No. 2, 1996 (pp. 79-82).
Argenta, Louis C., et al., "Vacuum-Assisted Closure: A New Method for Wound Control and Treatment; Clinical Experience", Ann Plas Surg 1997;38:563-577 (Dec. 10, 1996).
Aubrey, D.A., et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University. Cheboksary, USSR 1986) pp. 94-96 (with English translation).
Biblehimer, Helen L., "Dealing with a Wound that Drains 1.5 Liters a Day," RN, Aug. 1986, pp. 21-23, USA.
Bier, A., Hyperemia as a Therapeutic Agent, Ed. Dr. Gustavus M. Blech, A. Robertson & Co., Chicago 1905.
Braglina, I.O., et al. "Russian Chemical Bulletin", Dec. 31, 1983.
Brubacher, Lynda L., "To Heal a Draining Wound". RN, Mar. 1982, pp. 30-35, USA.
Bucalo et al "Inhibition of Cell Proliferation by Chronic Wound Fluid," Wound Repair and Regeneration. Miami, 1993, pp. 181-186.
Chariker, M.E., et al, "Effective Management of Incisional and Cutaneous Fistulae with Closed Suction Wound Drainage," Contemporary Surgery. Jun. 1989, pp. 59-63 vol. 34 USA.
Chintamani, et al., "Half versus full vacuum suction drainage after modified radical mastectomy for breast cancer—a prospective randomized clinical trial". Research Article (Jan. 27, 2005), 1-5.
Costunchenok, B.M., et al., Effect of Vacuum on Surgical Purulent Wounds, *Vestnik Chirurgia* Sep. 18-20, 1986, (in Russian with English translation).
Davydov, Y.A., etal., The Bacteriological & Cytological Assessment of Vacuum Therapy of Purulent Wounds, Vestnik Chirurgia 1988, Oct. Edition 48-52 (in Russian with English translation). 1987.
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.
Davydov et al. "Pathogenic Mechanism of the Effect of Vacuum Therapy on the Course of the Wound Process" pp. 43-46 (Dec. 1990).
De Lange, M.Y. , et al., "Vacuum-Assisted Closure: Indications and Clinical Experience", Eur J Plast Surg (2000) 2:178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
Fleischmann et al., Vacuum Sealing: Indication, Technique, and Results, Eur J Orthop Surg Traumatol, (1995) 5:37-40.
Fleischmann, W. Wund Forum Spezial, "Vakuumversiegelung zur Behandlung von Problemwunden" (with English translation: Vacuum Sealing for Treatment of Problematical Wounds), *IHW* '94, 6 pages.
Garcia-Rinaldi, R., et al., Improving the Efficiency of Wound Drainage Catheters, *Amer. Journ. of Surg.*, Sep. 1975, 130, 372-373.

(56) References Cited

OTHER PUBLICATIONS

Hartz, R.S., et al., Healing of the Perineal Wound, Arch. Surg., Apr. 1980, 115, 471-474.
Health Technology, Literature R., "Vacuum Assisted Closure Therapy for Wound Care", Health Technology Literature Review (Dec. 2004), 3-59.
Jeter, K. "Managing Draining Wounds and Fistulae: New and Established Methods" Chronic Wound Care pp. 240-246, 1990.
Johnson, F.E, An Improved Technique for Skin Graft Placement using a Suction Drain, Surgery, Gynecology & Obstetrics, Dec. 1984, 159(6), 584-585.
Kalypto Medical, NPD 1000 Product Brochure (publication date unknown, believed to be Nov. 2010).
Kalypto Medical, NPD 1000 Negative Pressure Wound Care System, Clinician & Patient Instructions for Use (publication date unknown, believed to be Feb. 2010).
KCI, Inc., If It's Not V.A.C. Therapy, It's Not Negative Pressure Wound Therapy, *KCI Brochure*, Jan. 2005, 1-5.
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Landes, R.R. and I. Melnick, An Improved Suction Device for Draining Wounds, *Arch. Surg.*, May 1972, 104, p. 707.
Linden van der, Willem, Randomized Trial of Drainage After Cholecystectomy, Modern Operative Techniques, Voluje 141, Feb. 1981, pp. 289-294.
McFarlane, R. M., "The Use of Continuous Suction Under Skin Flaps", F.R.C.S.(c), vol. 1, pp. 77-86 (1958).
McLaughlan, James, Sterile Microenvironment for Postoperative Wound Care, The Lancet, pp. 503-504, Sep. 2, 1978.
Meyer, Weight-Loaded Syringe as a Simple and Cheap Alternative to Pumps for Vacuum-Enhanced Wound Healing, Plastic and Reconstructive Srug., Jun. 2005, 2174-2176 (Correspondence).
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Nakayama, Y., et al., "A New Method for the Dressing of Free Skin Grafts", Plastic and Reconstructive Surgery, Dec. 1990 pp. 1216-1219, UK.
Nursing75, Wound Suction: Better Drainage with Fewer Problems, Nursing, vol. 5, No. 10, Oct. 1975, pp. 52-55.
Prevena™ Incision Management System, Patient Guide. pp. 1-2, Jan. 2010.
Prevena™ Incision Management System, Clinician Guide, pp. 1-9, Jan. 2010.
Ramirez, O.M., et al., Optimal Wound Healing under Op-Site Dressing, Ideas and Innovations, 73(3), pp. 474-475.
Ranson, John H. M.D., Safer Intraperitoneal Sump Drainage, Surgery Gynnecology and Obstetrics, pp. 841-42, 1973 vol. 137.
Sames, C.P., Sealing of Wounds with Vacuum Drainage, *Br. Med. Journ.*, Nov. 5, 1977, p. 1223, Correspondence.
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, Ph.D., World Wide Wounds—Next generation of products for wound management—2002 (13 pages).

Svedman, P., "Irrigation Treatment in Split-Thickness Skin Grafting of Intractable Leg Ulcers," Scand J. Plast. Reconst. Surg., 19:211-213, 1985.
Svedman, P., "Irrigation Treatment of Leg Ulcers," The Lancet, Sep. 1983, 532-34.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.
Swift, et al, "Quorum Sensing in *Aeromonas hydrophile* and *Aeromonas salmoncida*: Identification of LuxRI Homologs AhyRI and AsaRI and Their Cognate N-Acylhomoserine Lactone Signal Molecules," J. Bacteriol., 179(17):5271-5281 (1997).
Teder and Svedman et al., "Continuous Wound Irrigation in the Pig," Journal of Investigative Surgery, 1990, vol. 3. pp. 399-407.
Tribble, David E. M.D., An Improved Sump Drain-Irrigation Device of Simple Construction, Archives of Surgery New York, pp. 511-513, 1972 vol. 105.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Venturi, Mark L., "Mechanisms and Clinical Applications of the Vacuum-Assisted Closure (VAC) Device", Am J Clin Dermatol (2005) 693, 185-194; Review Article (2005), 185-194.
Vijanto, J. and J Raekallio, Local Hyperalimentation of Open Wounds, Br. J. surg., 1976, 63, 427-430.
Wackenfors, A., et al., Effects of Vacuum-Assisted Closure Therapy on Inguinal Wound Edge Microvascular Blood Flow, *Wound Rep. Reg*, 2004, 12, 600-606.
Webb, New Techniques in Wound Management: Vacuum-Assisted Wound Closure, Journal of the American Academy of Orthopadic Surgeons, v. 10, No. 5, pp. 303-311, Sep. 2002.
Webster's Revised Unabridged Dictionary, published 1913 by C. & G. Merriam Co., definition of Flapper Valve. downloaded from Free Online Dictionary.
Westaby, S., et al., "A Wound Irrigation Device", The Lancet, Sep. 2, 1978, pp. 503-504.
Wooding-Scott, Margaret, et al., "No Wound is Too Big for Resourceful Nurses," RN Dec. 1988, pp. 22-25 USA.
Wound Suction, Nursing, Oct., 1975, USA pp. 52-53.
Wu, W.S., et al. Vacuum therapy as an intermediate phase in wound closure: a clinical experience, Eur J Past Surg (2000) 23: 174-177.
English Translation of First Chinese Office Action for Chinese Application No. 200880117352.8 dated Jul. 3,2012 in 17 pages.
International Search Report for PCT/GB2008/051088, dated Mar. 4, 2009.
International Search Report for PCT/GB2008/051090, dated Mar. 4, 2009.
International Search Report for PCT/GB2008/051089, dated Mar. 4, 2009.
Canadian Office Action for Canadian Application No. 2739605 dated Aug. 22, 2011 in 2 pages.
Kendall Ultec Hydrocolloid Dressing (4"×4"), product ordering page, web page downloaded Jul. 13, 2014.
Membrane Filters, in 16 pages, from website: http://www.advantecmfs.com/catalog/filt/membrane.pdf#page=11 (date unknown, but believed to be copyright 2001-2011).
Protz, Kerstin: "Modern Wundauflagen unterstutzen Heilungsprozess", Wundversorgung: Indikation und Anwendung, Geriatrie Journal, Apr. 2005, pp. 3333-3339, with translation.
U.S. Appl. No. 10/599,720, filed Oct. 6, 2006, Blott et al.
U.S. Appl. No. 12/192,000, filed Apr. 14, 2008, Hartwell et al.
International Preliminary Report on Patentability, re PCT Application No. PCT/GB2008/051088, dated May 25, 2010.
Smith & Nephew, "PICO Single Use Negative Pressure Wound Therapy System", spiral booklet, Mar. 2011, in 7 pages.

\* cited by examiner

VACUUM ASSISTED WOUND DRESSING

CROSS-REFERENCE TO RELATED APPLICATIONS

This application is a continuation application of U.S. application Ser. No. 12/744,055, filed May 20, 2010, which is a U.S. National Phase of the PCT International Application No. PCT/GB2008/051088 filed on Nov. 20, 2008, designating the United States and published on May 28, 2009 as WO 2009/066104, which claims priority to Great Britain Patent Application No. 0722820.8, filed Nov. 21, 2007. The disclosure of these prior applications is incorporated by reference in their entirety and should be considered a part of this specification.

BACKGROUND OF THE INVENTION

Field of the Invention

The present invention relates to a topical negative pressure (TNP) assisted wound dressing particularly, though not exclusively, for the treatment of wounds of relatively low area and/or relatively low volume.

The subject of this invention is an apparatus for the management of small to medium sized wounds that utilises a vacuum source but manages wound exudate in a traditional manner by utilising an absorbent self-cohesive material in the wound cavity. No fluid is exported from the locality of the wound cavity other than by local evaporation. In this manner, an extremely portable system, of minimal inconvenience to the wearer, can be generated.

Background to the Invention

TNP therapy has enjoyed relatively recent commercial success. WO9605873 and its family members describes a portable TNP therapy apparatus. The apparatus described mechanically supports tissue in the vicinity of the wound site and tissue mechanics and the rate of exudation from such sites requires a system such as that described in WO9605873 or as described in patents such as GB2378392 and WO2005/082435 which have remote waste receptacles to which wound exudate fluid is aspirated in order to cope with the volume of fluids generated in a relatively short time, less than that period in which a dressing would normally be left in place. However, for wounds of surface area below approximately 200 cm$^2$ or internal volumes below about 1000 cm$^3$ these solutions may not be the most appropriate since exudate volumes and exudate rates from these wounds may be managed by more traditional wound dressings, requiring dressing change every 3-7 days. The relatively small dimensions of such wounds do not make them attractive for the traditional TNP therapies disclosed in the prior art; these devices typically including a remote vacuum source, fluid transfer lumen and remote fluid collection receptacle, control and power source and are of dimensions and weight exceeding those convenient or discrete for the patient to carry.

The general principles of TNP apparatus described in the prior art comprise a fluid-permeable wound cavity filling element, a dressing for covering the wound and providing a reasonably air-tight seal around the wound, a drainage tube connecting the wound site and cavity filling element to the vacuum source via a fluid collection canister. The precise nature of the wound filling element has been the subject of much invention in this field. The mode of action of the apparatus is the application of negative pressure to the wound cavity, causing compression of the wound cavity filler and expansion of the surrounding tissue into the wound cavity. Wound exudate is drawn from the surrounding tissue, through the still porous cavity filler, along the drainage tube and into the remote collection receptacle. An important feature of the prior art is the ability of the wound cavity filler to remain sufficiently porous, when compressed under negative pressure, to allow fluid transport from the tissue to the drainage or aspirant tube. Porosity can be facilitated at the molecular level, for example in a hydrogel, or at the microscopic level, for example in a hydrocellular foam. To facilitate fluid flow, a hydrophobic filling has been deemed particularly desirable by workers in the field and absorbent fillers as being particularly undesirable due to their hindering fluid transport.

In contrast to the principles of TNP therapy, the general principle of traditional wound dressings is the localisation of wound exudate at the locality of the wound, either within the wound cavity or in close proximity to the surface. For this purpose, extremely absorbent materials are desirable that retard the free flow of fluid, preferably absorbing the fluid and localising it. Aquacel (trade mark) made by ConvaTec Ltd is an example of a non-woven dressing that absorbs substantial quantities of fluid and effectively locks it in the dressing. Allevyn (trade mark) made by Smith & Nephew Ltd is an example of a foam dressing that absorbs substantial quantities of fluid while allowing rapid transpiration through a high moisture vapour permeable top-film.

SUMMARY OF SOME EXEMPLIFYING EMBODIMENTS

In summary, the prior art deals exclusively with vacuum assisted fluid transport away from the site of the wound. A very broad range of wound cavity filling and contacting elements have been described and exemplified in the prior art, including materials commonly used in traditional wound care dressings. Without exception in these cases, the cavity filling and wound contacting elements act as a conduit for the transport of fluid from the wound per se to a remote collection canister via an aspirant tube connected to a vacuum source.

An object of the present invention is to overcome or reduce the limitations of the prior art for the management of wounds of low surface area, particularly those below approximately 200 cm$^2$ or internal volumes below 1000 cm$^3$, while not resorting to the exclusive use of traditional absorbent dressings. A further object of the present invention is to overcome or minimise the problem of vacuum device portability.

According to a first aspect of the present invention there is provided apparatus for the application of topical negative pressure therapy to a wound site, the apparatus comprising: a wound contacting element for retaining wound exudate fluid therein; a wound covering element that provides a substantially airtight seal over the wound contacting element and wound site; a vacuum connection tube connecting the wound contacting element to a vacuum source; and a vacuum source connected to a distal end of the vacuum connection tube.

The wound contacting element essentially blocks liquid transport beyond itself under pressures between atmospheric pressure and 200 mmHg below atmospheric pressure. Preferably, the wound contacting element material blocks liquid transport beyond itself at pressures of up to 250 mmHg below atmospheric pressure.

This invention concerns apparatus including a dressing for the management of wounds. In contrast to current therapies and prior art in the field of TNP therapy, the invention provides a system that, while exposing the wound to the many benefits of TNP, does not allow the export of wound fluid from the confines of the wound cavity. The apparatus relies upon a wound contacting element that does not allow the transport of fluid beyond itself under the range of negative pressures being applied to the wound.

A particular advantage of the apparatus according to the present invention is that confinement of wound fluid to the immediate vicinity of the wound enables the provision of an extremely small and light and consequently highly portable vacuum source and a convenient simple coupling and decoupling means of the vacuum source to the wound site dressing and which overcome significant limitations in the usability and portability of prior art apparatus.

In the present specification the term 'wound contacting element' means the portion of the apparatus/dressing filling the wound cavity or covering the wound. The nature of the wound contacting element is not restricted, provided that its composition or structure is able to essentially block the flow of exudate away from itself under the pressure range specified above.

For example, the wound contacting element may include a liquid-triggered valve that closes when it becomes in contact with a liquid. Such a valve may be situated proximate to the vacuum tube connection point at the wound covering element. Thus, when contacted by liquid the valve closes and no liquid is transported by the vacuum tube. The valve may be an electromechanical valve or a smart valve comprised of a water-absorbent material that expands to close within a constriction upon contact with liquid. The water-absorbent material may be placed within a restricted aperture within the valve. The wound contacting element positioned between such a valve and the wound may be absorbent or non-absorbent but may preferably be absorbent. The filling, in this embodiment, may be any medically-suitable composition such as, for example, a gauze, a foam, a woven, a non-woven, knit or moulded material.

Alternatively, the wound contacting element may comprise entirely, or in part, a suitable material structured such that it can absorb wound exudate but does not allow transmission of this fluid to the vacuum tube. This configuration is defined by two parameters: the aperture of the exit(s) from the material constituting the wound contacting element and the mechanical integrity of the material when wet. For example, an absorbent material that becomes laden with exudate must not itself be displaced along the vacuum connection tube. This is a particular problem with particulate or fibrous so-called superabsorbent materials, for they can pass, even when fully saturated with fluid, through very small apertures of a size below which vacuum levels cannot be efficiently maintained. In effect this means that the narrower the tube transmitting the vacuum, the greater the loss in vacuum pressure with distance from the vacuum source, which loss in negative pressure is negligible for macroscopic bores but can be significant as bores reduce below 1 mm diameter. To overcome these problems, an absorbent material with substantially enhanced self-cohesive properties compared to those currently available is described in our co-pending patent application GB0719065.5 of common ownership herewith.

When an absorbent material is included in the wound contacting element, the absorbent material not necessarily acting as a fluid transport blocking element, the material may preferably be capable of absorbing more than 5-times its own weight in fluid, more preferably more than 10-times its own weight in fluid and more preferably still more that 15-times its own weight in fluid. Such high w/w fluid absorbency may be desirable so that the wound can be initially dressed with a low weight material thereby reducing stress on the wound and the patient.

One group of materials particularly suited for this purpose are so-called superabsorbent materials, for example, those based on polycationic or polyanionic polymers. Superabsorbent polyanionic polymers include polyacrylic acid salts and polyacid derivatives of polysaccharides, such as carboxyalkylcellulose, or structural derivatives. Preferably, when the material is polyanionic, it may be a polyacrylic acid salt or derivative or carboxymethylcellulose or derivative. Preferably, when the material is polycationic, it may be chitosan-based, more preferably a carboxyalkylchitosan or derivative, even more preferably carboxymethylchitosan.

One particularly preferred material is a superabsorbent material capable of self-coalescence upon fluid absorption (see our GB0719065.7 the content of which is included herein by reference). These materials are able to effectively block the transport of liquid beyond their boundaries and also do not themselves flow or disaggregate under the influence of negative pressure or at the levels of externally applied physical stresses resulting from the negative pressure within a wound cavity.

A preferred material attribute may be the ability to achieve rapid haemostasis in the event of bleeding in the wound site.

A further preferred material attribute may be the ability to kill pathogens, such as bacteria or fungi, which come into contact with it. Preferably the material is inherently antimicrobial.

Carboxyalkylchitosan-based materials are suitably both haemostatic and antimicrobial.

The wound contacting element material can be provided in any form suitable to enable fluid ingress and absorption but to block the flow of fluid away from the wound contacting element. Suitable designs include dispersions of superabsorbent particles within a network of wicking fibres (as utilised in diapers, for example) or reticulated or discontinuous material comprising the superabsorbent material, such as open celled foams, knits, laminates, woven or non-woven materials. Preferably, the material may be in the form of a non-woven sheet for application to largely two-dimensional wounds or non-woven balls for application to largely three-dimensional wound cavities.

The wound covering element may be any material substantially impermeable to the flow of liquid, but may or may not be substantially permeable to the transmission of water vapour. The wound covering element is preferably a highly conformable transparent material which may optionally be coated with, or be manufactured such that, the side contacting the wound contact element and the patient's skin may be considered adhesive to the skin. Here, adhesive is taken to mean able to stay in place in the absence of negative pressure. Suitable materials for the manufacture of a highly conformable transparent wound covering include polyurethanes, polyolefins, polyacrylates, silicone-based polymers or composites comprising any combination of these materials.

The wound covering element may be a traditional wound dressing, for example composed of an absorbent foam, for example, Allevyn (trade mark) made by Smith & Nephew Medical Limited or non-absorbent film such as Tegaderm (trade mark) made by 3M Inc.

The wound covering element may be optionally provided with a means of connecting the vacuum connection tube with the wound covering element by, for example, a central or radial aperture or apertures in the wound covering element. The wound contacting element may be connected, via the wound covering element, to the vacuum connection tube by any means known to the skilled person including luer fittings such as commercially available valves and ports, magnetic couplings or adhesive sheet or tape. The connection of the vacuum tube to the wound covering element may preferably be achieved via a non-adhesive elastomeric cup positioned at the end of the vacuum connection tube and a pressure-sensitive valve positioned in the wound covering element itself. The pressure-sensitive valve may open when a pressure differential of a specified magnitude exists over its two surfaces such as between 5 and 200 mmHg, for example. The material comprising the elastomeric cup and pressure-sensitive valve may preferably be a silicone-based material. It is desirable that the coupling system is suitable for repeated coupling and uncoupling, as convenient for the patient.

Optionally, these coupling elements may be impregnated or coated with antimicrobial materials including, but not restricted to, antibiotics, silver compounds or materials, iodine-based formulations, polyhexamethylene biguanide, triclosan or chlorhexidine. Preferably, the elements may be coated with silver clusters.

The vacuum connection tube may be any of appropriate mechanical properties and bore for the transmission of negative pressure from the vacuum source to the wound contacting element. However, dependent upon the configuration of the wound contacting element, the bore of the tube may be such that it is incapable of transmitting dry or hydrated components of the wound contacting element. The tubing may be as conformable and light weight as possible and may be coiled or linear. The tubing may be single or multi-lumen, or a combination of lumens, and may optionally split and or rejoin to form separate tubular elements for the management of a single wound site or multiple wound sites. The tubing may be opaque or transparent.

The wound contacting element and wound covering element may be optionally combined into a single element.

The wound covering element and vacuum connection tube may optionally be combined into a single element.

The wound contacting element, wound covering element and vacuum connection tube may be optionally combined into a single element.

The vacuum source may be any available and may be optionally mechanically powered by, for example, a compressed spring and comprise a syringe as the vacuum generating means as is known in the prior art; or electrically powered, for example a vacuum pump. Preferably, the vacuum source may be capable of generating vacuums in the range of −10 mmHg to −250 mmHg relative to atmospheric pressure. More preferably, the vacuum source is a vacuum pump capable of generating vacuums in the range of −10 mmHg to −250 mmHg relative to atmospheric pressure. The pump may generate a vacuum by any convenient means; diaphragm pumps, peristaltic pumps, Venturi-effect pumps and other displacement pumps may be suitable for this purpose.

The vacuum source may preferably be below 500 g in weight, more preferably below 100 g in weight and even more preferably below 50 g in weight.

In cases where the vacuum source is electrically powered, the power source may be mains supplied, a battery supply or a locally generated supply such as a clockwork generator, a solar cell, a thermo cell or a kinetic autorelay type of power source. Preferably the power source may be a battery.

In cases where the power source is a battery, the battery may be disposable or rechargeable. When the battery is rechargeable, recharging may be achieved via a charging station for the vacuum housing or for the battery itself. Battery life may be preferably longer than 12 hours, more preferably longer than 24 hours and even more preferably longer than 72 hours. The battery may preferably be below 100 g in weight, more preferably below 50 g in weight.

The power and vacuum sources may be housed separately or together. Preferably they are housed together. When housed, the combined weight of the power and vacuum source and housing may be preferably less than 1 kg, more preferably less than 500 g, more preferably still less than 200 g. The housing may be of any geometry but is preferably adapted so as to be convenient for the patient and/or carer to handle and carry. It may also preferably be of dimensions below 15×15×6 cm.

The apparatus of the first aspect of the present invention may be applied to wounds for their management. The general principle of the apparatus is the application of the wound contacting element to the wound, covering the wound contacting element with the wound covering element and coupling the wound contacting element to a vacuum source via a vacuum connection tube. As mentioned above, two or more of these elements may be provided as a single entity. Preferably for largely two-dimensional wounds, the wound contacting element and the wound covering element may be a single entity. This combined entity may contain the pressure-sensitive valve in its top surface and may be attached to the perimeter of the wound by appropriate means. Attachment of the dressing to a patient may be achieved by the application of negative pressure alone, in the absence of a bonding means or may be achieved via a bonding means. Attachment may preferably be achieved by a bonding means, for example a pressure sensitive adhesive applied to the skin contacting surface of the wound covering element. When the bonding means is a pressure sensitive adhesive, it may preferably be a poly(acrylate)- or silicone-based formulation.

According to a second aspect of the present invention there is provided apparatus for the application of topical negative pressure therapy to a wound site, the apparatus comprising: a wound covering element that provides a substantially airtight seal over the wound; a vacuum connection tube connecting the wound covering element to a vacuum source; a vacuum source connected to a distal end of the vacuum connection tube; the wound covering element having valve means associated therewith which permits only fluid flow out of a wound cavity defined by the wound covering element and the wound.

When the wound contacting element and the wound covering element are in place, the vacuum source is activated and the vacuum connection tube, preferably attached to the vacuum source, may be connected to the wound covering element via an aperture or valve in the wound covering element. At any point during the application of negative pressure therapy, the coupling of vacuum connection tube to the wound covering element can be reversibly broken and re-established at the convenience of the patient or carer.

In an embodiment of the apparatus according to either the first or second aspects of the present invention the dressing wound covering element may comprise a one-way valve as mentioned above, the valve essentially being able to allow fluid in the form of air to be withdrawn from the wound cavity defined by the wound covering element via the vacuum connection tube. As mentioned above the vacuum connection tube may preferably be repeatably connectable and disconnectable to the dressing/wound covering element without damage thereto such that the vacuum source may be removed by the patient and the dressing left in place but sealed against the ingress of bacteria and potential infection, for example, by the presence of the one-way valve in the wound covering element. The one-way valve means may be a simple plastics material self-sealing valve as are available commercially for many diverse applications outside of the field of TNP therapy such as those sold under the trade mark "miniValve" by Mini Valve International, for example.

Desirably the vacuum connection tube may be attached to the dressing/wound covering element by non-adhesive means so as to facilitate repeated connection/disconnection thereof without damaging the wound covering element film material. In this regard the vacuum connection tube may be connected by "sucker" means at the dressing end of the vacuum connection tube, the sucker means being, for example, in the form of a cup-shaped, domed or bell-shaped conformable plastics material member which is in fluid communication with the vacuum connection tube and which member which may be placed over the valve means in the wound covering element and seal with surrounding wound covering element material, the sucker means being held in place on the dressing/wound covering element by the vacuum generated by the vacuum source itself. Disconnection of the vacuum connection tube may then be effected merely by turning off the power source to the vacuum source or by breaking the seal of the sucker by lifting its edge (NB the sucker can easily be removed by this intentional manipulation but cannot easily be accidentally dislodged by vertical extensive force e.g. pulling on the vacuum connection tube).

When the wound contacting element becomes saturated with wound exudate, the vacuum connection tube can be disconnected and the wound contacting element and wound covering element (or a physical combination of the two) can be exchanged for a new set.

Wounds suitable for management by the apparatus that is the subject of this invention include injuries to soft and hard tissue, including the skin, muscle, cartilage, tendons, bone and internal organs.

In the second aspect of the invention a wound contacting element of highly absorbent material may not be present and wound exudate may be aspirated from the wound cavity to a remote waste receptacle by the vacuum source.

BRIEF DESCRIPTION OF THE DRAWINGS

In order that the present invention may be more fully understood examples will now be described by way of illustration only with reference to the accompanying drawings, of which.

DETAILED DESCRIPTION OF SOME EXEMPLIFYING EMBODIMENTS

Referring now to the drawings and where the same features are denoted by common reference numerals.

Figure 1:
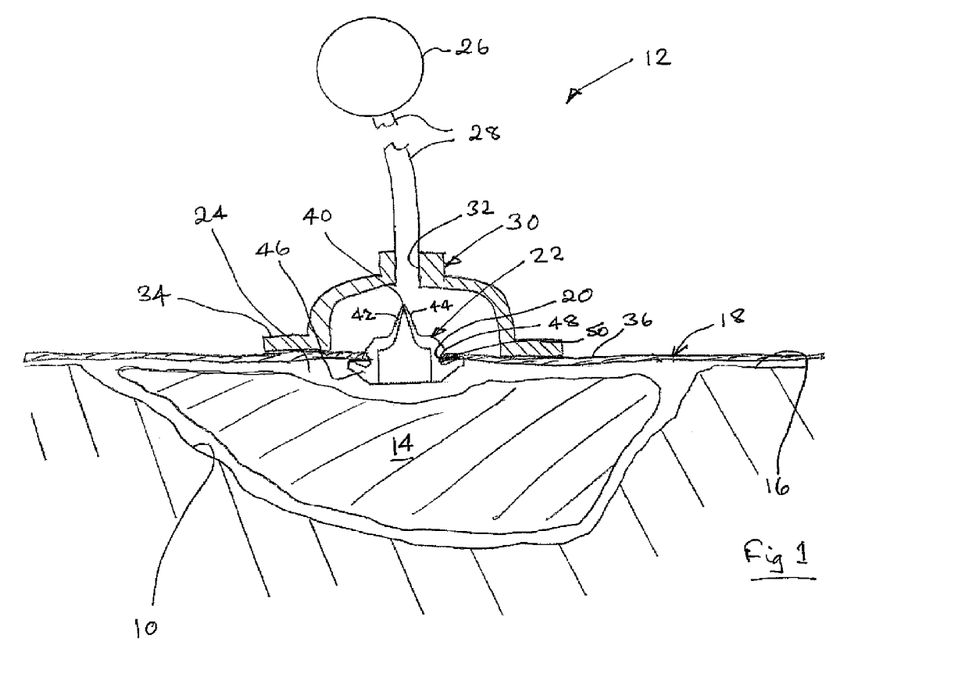
FIG. 1 shows a schematic cross section of an embodiment of apparatus according to the present invention and a wound being treated by TNP therapy.

FIG. 1 shows a schematic cross section through a wound 10 having an embodiment of apparatus 12 according to the present invention applied to it for the purpose of TNP therapy of the wound. The wound 10 has a wound contacting element 14 placed in the cavity defined by the wound, the wound contacting element being roughly level with surrounding sound skin 16. A wound covering element 18 is applied over the wound to contact and seal with the surrounding sound skin by means of a layer of pressure sensitive adhesive (not shown) coated onto the skin contacting surface of the wound covering element material. The wound covering element 18 has an aperture 20 in the area above a part of the wound and the wound contacting element 14. A one-way valve 22 is positioned in the aperture 20 to permit fluid in the form of air to be extracted from the wound cavity 24 defined by the wound covering element 18 and the wound 10 itself. A vacuum source 26 in the form, in this example, of a battery powered vacuum pump is connected to the wound cavity by a vacuum connection tube 28 and a cup-shaped connection member 30 having an aperture 32 therein to accept the end of the vacuum connection tube 28. The cup-shaped member 30 has a flange portion 34 which seats onto the upper surface 36 of the wound covering element 18 material and seals therewith. The valve 22 has an orifice 40 which is normally closed due to the resilience of the material from which it is moulded, for example, silicone plastics based material. The orifice 40 is in the form of a slit normally closed by two lips 42, 44 (the shape of the valve orifice may be likened to a flat bladed screwdriver and the valve orifice 40 in FIG. 1 runs normal to the plane of the page). The valve 22 is initially held in and sealed to the wound covering element material 18 by a flange portion 46 bearing against the underside of the wound covering element 18 material and a circular shoulder 48 and recess 50 which is held in the aperture 20. To evacuate the wound cavity 24, the vacuum pump 26 is started and the cup-shaped member 30 placed on the wound covering element material above the valve 22 and the reduction in pressure within the wound cavity 24 causes the cup-shaped member 30 to be sealed securely to the dressing by the excess pressure of the surrounding ambient air. As the vacuum in the wound cavity develops, the wound covering element 18 is pushed down against the wound contacting element 14 by ambient air pressure and the wound contacting element 14 compressed against the wound surface to apply TNP therapy thereto.

Whilst it is perfectly feasible for the lower surface of the flange portion 34 of the cup-shaped member 30 to be adhesively coated and to be so retained on the wound covering element material, in this example retention of the vacuum connection tube 28 to the wound dressing is solely by ambient air pressure as described above. In case the patient wishes to detach the vacuum pump 26 and leave it behind this may simply be achieved by turning off the pump 26 and allowing the vacuum to degrade and removing the cup-shaped connection member 30. In this case the valve 22 is self-sealing prevents access of bacteria and the like to the wound cavity 24.

The valve 22 exemplified above is a miniValve (trade mark) supplied by Mini Valve International. However, this valve is merely exemplary and many other types of suitable valves are available commercially.

For example International Patent Application No PCT/EP2008/063046 discloses a composition which coalesces on hydration and which can be used to provide a valve which closes upon contact with liquid. The application is included fully herein by way of reference but briefly discloses a suitable composition that enables a new physical transformation. The physical transformation in question involves the conversion of a first stable physical geometry into a second stable physical geometry upon hydration, wherein hydration enables the self-coalescence (fusion) of spatially separated elements or surfaces of the first stable physical geometry.

Each geometry is physically stable. Thus, immersion of the first stable physical geometry in excess solution results in conversion to the second stable physical geometry without significant loss of the material mass by dissolution. That is, the second stable geometry is insoluble, or has only very limited solubility, in the excess solution. The second stable physical geometry is, at least substantially, self supporting such that it is able to retain its shape when is excess solution, or when removed therefrom. In typical preferred forms in the second stable physical geometry the material of the invention is a gel or gel like material.

A feature of the composition is the physical homogeneity of the object in both the first and second physical geometries.

The novel transformation is enabled by construction of the object, at least in part, from materials that can exist in physically stable forms in the dry state and the hydrated state. Furthermore, the hydrated state of the material must be sufficiently self-cohesive, even when immersed in excess solvent, to enable fusion to occur. This, we believe, is a property unique to a limited range of states of matter, some of which we prepare to exemplify this invention.

In broad terms the composition of matter when formed into an object of suitable geometry, can self-coalesce upon hydration in a suitable solvent.

According to a first aspect of the composition there is provided a high molecular mass cationic polymer material having a first state which includes at least two separate but adjacent surfaces and a second state in which the polymer consists of a homogeneous body, wherein the material transitions from the first state to the second state upon hydration.

Thus, on hydration the material expands and the surfaces merge or coalesce to result in a body of self supporting material, typically a gel or gel-like material, which has uniform properties in any dimension. Surfaces and other boundaries within the body of material are absent. Furthermore the body of material is insoluble, or at least of limited solubility in the hydrating solvent and is able to retain its physical geometry under leading (for example gravity).

The term 'suitable geometry' is taken to describe an arrangement where separate (for example spatially separate, but not necessarily physically separate) elements or surfaces of the object are sufficiently proximate to enable coalescence upon hydration-induced expansion.

The term 'suitable solvent' is taken to describe a fluid (liquid or gas) that can be absorbed be the object, causing expansion and a change in the physical properties of the object (e.g. surface energy). The suitable solvent is typically and preferably an aqueous medium.

The term 'self-coalesce' is taken to describe the transformation of two or more spatially separated physically homogeneous elements into a single physically homogeneous element or of fusion of previously spatially separated surfaces of the same element.

Suitable compositions of matter from which objects can be formed are those comprised, entirely or in part, of high average molecular weight cationic polymers including zwitterionic (carrying both anionic and cationic charge) polymers with a cationic charge bias. The cationic polymer may be, or may be a derivative of, a synthetic or a naturally occurring polymer. Preferably, the cationic polymer is one carrying amine functionality. More preferably, the cationic polymer is a polysaccharide. More preferably still, the cationic polymer is chitosan or a derivative of chitosan. The chitosan may be derived from any source, marine or fungal, and is preferably of a weight average molecular weight (Mw) exceeding 10 kDa (kilodaltons), more preferably exceeding 100 kDa and most preferably exceeding 200 kDa.

Where the polymer is a derivative of chitosan, it is preferably a carboxylated derivative. More preferably, it is a carboxyalkyl derivative of chitosan. More preferably still, it is a carboxymethyl derivative of chitosan. The carboxymethyl derivative of chitosan is preferably of a weight average molecular weight exceeding 50 kDa, more preferably exceeding 100 kDa, especially exceeding 500 kDa, more especially exceeding 600 kDa and especially 700 kDa or more.

Carboxymethylation is preferably achieved using known reagents: a base and chloroacetic acid or preferably a neutral salt of chloroacetic acid such as sodium chloroacetate. Preferably, the reaction is carried out in a single step: chitosan fibres or (less preferably) particles being immersed in a solution of reagents or vice versa. Suitable reaction solvents include mixtures of an alcohol with water. The alcohol may be any known but is preferably a non-solvent for chitosan and carboxymethylchitosan, for example isopropanol. The base may be any known but is preferably a water-soluble inorganic base such as sodium hydroxide or potassium hydroxide, preferably sodium hydroxide.

According to a second aspect of the composition there is provided a method of preparing high molecular mass carboxymethylchitosan comprising the steps:
a. mixing chitosan with a solution of a base and chloroacetic acid, or a neutral salt thereof, dissolved in a reaction solvent comprising a mixture of an alcohol and water;
b. allowing the reaction to proceed at ambient temperature for at least 8 hours whilst ensuring adequate exposure of the chitosan to the reaction solvent;
c. when the reaction is complete, washing the reaction product in excess alcohol-containing solvent;
wherein the volume (in milliliters) of the reaction solvent is at least 20-times the mass (in grams) of chitosan.

A high molecular mass carboxymethyl chitosan preferably comprises a carboxymethyl chitosan having a mass of at least 500 kDa, more especially at least 600 kDa and especially 700 kDa or more.

In one preferred embodiment the volume of reaction solvent (in milliliters) exceeds the mass of chitosan (in grams) by more than 20 but less than 70-times, more preferably by more than 30-times but less than 40-times.

In another preferred embodiment the mass of sodium chloroacetate exceeds the mass of chitosan by not more than 2-times, more preferably by not more that 1.2-times.

In a preferred embodiment, the alcohol of the reaction solvent is isopropanol.

In further preferred embodiments the reaction is carried out at ambient temperature for a period of at least 8 hours, more preferably for at least 15 hours and even more preferably for at least 18 hours.

In a particularly preferred embodiment, the alcohol of the reaction solvent is isopropanol, the mass of sodium chloroacetate is not more than twice (more especially not more than 1.2 times) the mass of the chitosan and the reaction is allowed to proceed for at least 8 hours.

When the chitosan is provided for reaction in powder or fibre form, this material should be adequately exposed to the turbid reaction solvent throughout the duration of the reaction. This process can be facilitated by any means known to the artisan but can be simply achieved by rolling the reaction vessel, for example.

When the reaction is complete, reaction by-products detrimental to the stability of the product, such as sodium chloride or sodium hydroxyacetate, should be removed to the maximum extent feasible. To achieve this, the reaction product is washed, preferably in one or more steps, in excess solvent comprised of at least 60 parts alcohol (such as ethanol) and 40 parts water (60:40).

More than one washing step is preferred and, when this is the case, the first wash step has preferably a higher water content than subsequent steps, with water content decreasing in every wash step. For example, a suitable two-step wash procedure involves a first wash in excess solvent comprised of at least 60 parts ethanol and 40 parts water (60:40) and a second wash in excess solvent comprised of at least 90 parts ethanol and 10 parts water (90:10).

Thus in a preferred embodiment the reaction product is washed in a plurality of washing stages, each employing an excess of a solvent comprising alcohol and water, wherein in each succeeding stage the solvent consists of a higher proportion of alcohol. Preferably the alcohol is ethanol It is essential that wash solvents always includes some water to avoid excessive dehydration of the product, which can result in brittleness.

The composition of the wash solvent may include any suitable alcohols such as ethanol, isopropanol or methanol. Ethanol is preferred.

The product resulting from washing and solvent removal can be sterilised by methods typical for the sterilisation of medical devices, for example gamma-irradiation, electron-beam irradiation or ethylene oxide treatment.

Prior to radiation-based sterilisation, the washed reaction product should be adequately solvent-free. This can be achieved by any drying process known to the skilled artisan. A preferred drying process is conducted at temperatures not exceeding 40° C., more preferably not exceeding 30° C. Preferably, solvent removal is achieved by placing the material under a sub-atmospheric pressure.

The pressure is preferably less than 500 mbar, more preferably less than 1000 mbar. The duration of the drying process, when achieved by vacuum drying, preferably exceeds 8 hours, more preferably exceeding 12 hours.

The weight average molecular weight of the material following washing and radiation sterilisation is preferably greater than 120 kDa, more preferably greater than 130 kDa and after washing and ethylene oxide sterilisation is preferably greater than 400 kDa, more preferably greater than 500 kDa. It is important that these molecular weights are obtained to avoid mechanical integrity problems in the final product and dissolution problems when exposed to fluid.

Additives and co-components can be added at any stage of the above process, prior to terminal sterilisation. These agents may be any suitable for a topical or internal medical application, such as analgesics, anaesthetics, antimicrobial agents, anti-cancer agents, nicotine or nicotine substitutes or other synthetic or naturally-derived pharmaceuticals including peptides, proteins such as growth factors or retardants, enzymes (e.g. those facilitating tissue debridement), DNA or RNA fragments.

When the additive is an antimicrobial agent, it may be for example: silver or silver compounds, iodine or iodine compounds, quaternary amine-based antimicrobials such as polyhexamethylenebiguanide or chlorhexidene, antibiotics such as gentamycin, vancomycin or a peptide-based agent.

When silver is introduced into the formulation, and the formulation is carboxymethylchitosan-based, addition is preferably achieved by immersion in a solvent mixture of a similar composition as that applied during the carboxymethylation process.

In a third aspect, the composition can be used to provide a method of fusing two or more solid surfaces, wherein the surfaces are initially separate (in particular, spatially separated) but adjacent surfaces of one or more object(s) comprising a self-coalescing material as herein described, notably the high molecular mass polymer material of the first aspect of the invention. The method comprises the step of immersing said surfaces in an aqueous medium and thus hydrating and expanding the self-coalescing material. In one embodiment, the surfaces are initially spatially separated surfaces of the same object. Alternatively, the surfaces are initially spatially separated surfaces of different objects. These alternatives are not mutually exclusive. The surfaces may be the surfaces of fibres, for example in a woven or, more especially, a non-woven fibrous material. In such materials, the surfaces may have portions which are spaced apart and portions which, while being separate, are in contact.

Objects fabricated from the compositions defined above, and suitable for the method, need to be suitably designed to enable coalescence upon hydration. For example, an isolated linear object would not have the opportunity to self-coalesce upon hydration. In contrast, a pair of isolated but adjacent linear objects would have the opportunity to swell and coalesce upon hydration. In this context, 'adjacent' means located within about 10 mm of one another. Thus, suitable objects can be defined as containing, at least in part, spatially separated elements or surfaces located within about 10 mm of one another. Preferably, the spatially separated elements or surfaces are located within 5 mm of one another. More preferably, the spatially separated elements or surfaces are located within 1 mm of one another. In some cases, for example fibre based materials, at least parts of adjacent surfaces may be in contact.

Preferred physical formats that meet the above description are fibre-based materials such as woven and non-woven materials. Other suitable formats include knits, open-celled foams and laminates including corrugated materials. More complex arrangements can be fabricated by methods known to one skilled in the art, such as lithography, micromachining and electrospinning. The composition and its uses is not restricted to formats of high open area but includes solid monoliths. Fibre based materials are preferred and fibre-based non-woven materials are particularly preferred.

The composition in use is not restricted to objects consisting exclusively of self-coalescent material, but includes composites, for example composites of common medical device formats and self-coalescent material and surface-coatings, for example implantable metal- or biomaterial based devices including soft-tissue substitutes and joint implants. Composites suitable for topical and internal wound management include those combining polyurethane based materials, such as foams, slabs and films with self-coalescent materials, for example in powdered or, more especially, fibrous form.

When devices comprised, at least in part, of the compositions are immersed in a fluid, they absorb fluid, become swollen and self-coalesce across contact points. Use is not restricted to specific compositions or specific fluids, but in preferred forms and for preferred end-sues, the fluid is most preferably water based. For example, in the case of carboxymethylchitosan-based materials, the fluid is preferably water based. Examples of water based fluids include water or a solution of water, such as saline or a biologicallyderived fluid such as whole blood, blood plasma, serum, saliva, wound exudate or bone marrow aspirate.

The novel material properties of the described self-coalescing materials can be exploited in a range of applications, for example in irreversible fluid valving systems and moulding materials.

EXAMPLES

Example 1

Generation of Self-Coalescing Carboxymethylchitosan Fibres

A) Synthesis

Immediately prior to reaction, sodium chloroacetate (1.75 g) was dissolved in 4% aqueous sodium hydroxide solution (7 ml). This solution was added to isopropanol (45 ml) and shaken vigorously, resulting in a turbid suspension. This mixture was added to a vessel containing chitosan fibres (1.50 g), the container sealed and rolled at approximately 60 rpm for 18 hours.

B) Washing Steps

B1) After step A, the fibres were removed from the now clear reaction solvent and transferred to a vessel containing 99:1 ethanol:water (200 ml). The material was disturbed every 15 minutes for 1 hour, after which time the material was removed and physically dried by the application of hand pressure between several layers of absorbent material. Following gross drying, the material was vacuum dried at ambient temperature overnight.

B2) After step A, the fibres were removed from the now clear reaction solvent and transferred to a vessel containing 60:40 ethanol:water (200 ml). The material was disturbed every 15 minutes for 1 hour, after which time the material was removed and transferred to a second vessel containing 90:10 ethanol:water (200 ml). The material was disturbed every 15 minutes for 1 hour, after which time the material was removed and physically dried by the application of hand pressure between several layers of absorbent material. Following gross drying, the material was vacuum dried at ambient temperature overnight.

Example 2

Generation of Self-Coalescing Carboxymethylchitosan Fibres (Scale-Up)

Immediately prior to reaction, sodium chloroacetate (96.8 g) was dissolved in 4% aqueous sodium hydroxide solution (387 ml). This solution was added to isopropanol (2490 ml) and shaken vigorously, resulting in a turbid suspension. This mixture was added to a vessel containing chitosan fibres (83.0 g), the container sealed and rolled at approximately 60 rpm for 18 hours. After this time, the fibres were removed from the now clear reaction solvent and transferred to a vessel containing 99:1 ethanol:water (2000 ml). The material was disturbed every 15 minutes for 1 hour, after which time the material was removed and physically dried by the application of hand pressure between several layers of absorbent material. Following gross drying, the material was vacuum dried at ambient temperature overnight.

Example 3

Radiation Sterilisation of Self-Coalescing Carboxymethylchitosan Fibres

The material resulting from Example 1, step B2 was packaged in gas-permeable sterilisation pouches and sterilised by gamma irradiation at 30-40 kGy. The molecular weight of the material pre- and post-sterilisation was determined by gel permeation chromatography. The molecular weight prior to sterilisation was approximately Mw 700 kDa; the molecular weight post-sterilisation was approximately Mw 140 kDa. The molecular weight change in the material, although substantial, was such that the physical properties of the material were not significantly altered by sterilisation.

Example 4

Ethylene Oxide Sterilisation of Self-Coalescing Carboxymethylchitosan Fibres

The material resulting from Example 1, step B2 was packaged in gas-permeable sterilisation pouches and sterilised by ethylene oxide treatment. The molecular weight of the material pre- and post-sterilisation was determined by gel permeation chromatography. The molecular weight prior to sterilisation was approximately Mw 700 kDa; the molecular weight post-sterilisation was approximately Mw 575 kDa. The molecular weight change in the material was such that the physical properties of the material were not significantly altered by sterilisation.

Example 5

Water Absorbency of Self-Coalescing Carboxymethylchitosan Fibres

The material resulting from Example 3 (100 mg) was immersed in water (4 ml) for 1 minute and withdrawn. Excess liquid was allowed to drain and then the hydrated transparent mass was weighed. The material was calculated to absorb approximately 25-times its own mass in water without significant dissolution.

Example 6

Serum Absorbency of Self-Coalescing Carboxymethylchitosan Fibres

The material resulting from Example 3 (100 mg) was immersed in serum (4 ml) for 1 minute and withdrawn. Excess liquid was allowed to drain and then the hydrated transparent mass was weighed. The material was calculated to absorb approximately 13-times its own mass in serum without significant dissolution.

Example 7

Self-Coalescence of Carboxymethylchitosan Fibres in Water

The material resulting from Example 3 (100 mg) was immersed in water (4 ml) for 1 minute and withdrawn. Excess liquid was allowed to drain and then the hydrated transparent mass was allowed to stand for 4 hours. After this time, the individual fibres of the material had self-coalesced and the material was then effectively a homogeneous, elastic hydrogel, able to stably retain its physical geometry under loading (FIG. 2).

Example 8

Self-Coalescence of Carboxymethylchitosan Fibres in Serum

The material resulting from Example 3 (100 mg) was immersed in serum (4 ml) for 1 minute and withdrawn. Excess liquid was allowed to drain and then the hydrated transparent mass was allowed to stand for 4 hours. After this time, the individual fibres of the material have self-coalesced and the material as effectively a homogeneous, elastic hydrogel, able to stably retain its physical geometry under loading.

Figure 2A:
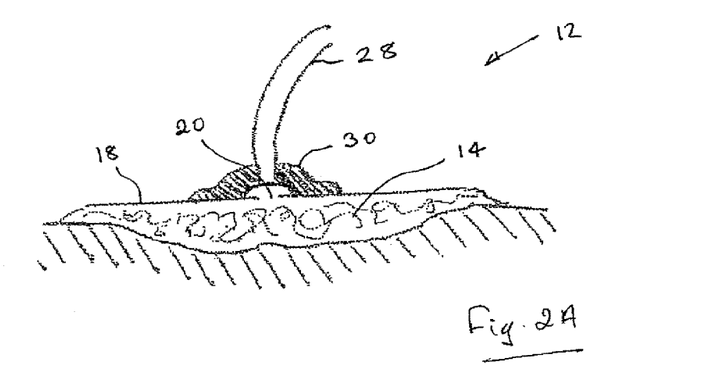
FIGS. 2A to 2C which show the arrangement of FIG. 1 simplified and the progression of saturation of a wound contacting element.
Figure 2B:
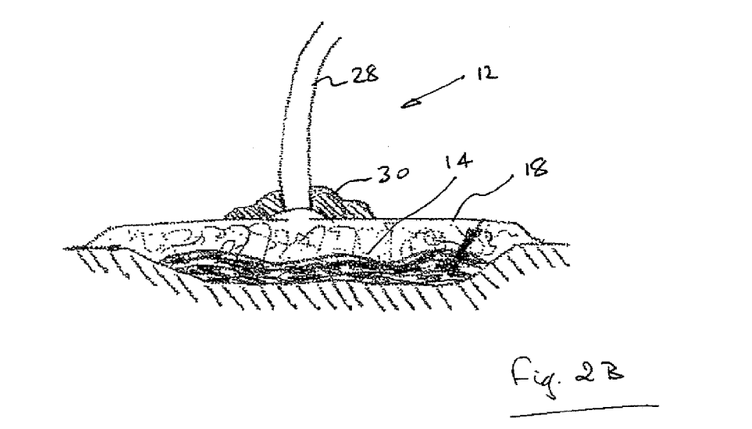
Figure 2C:
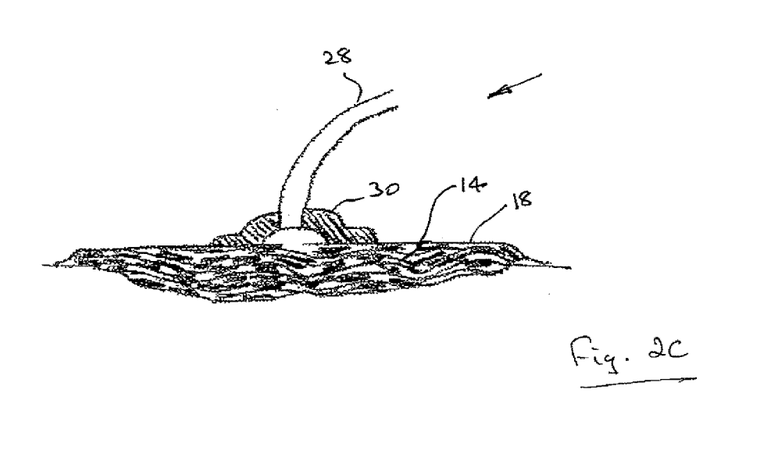

FIGS. 2A to 2C show stages in the absorption of wound exudate into the wound contacting element 14. The basic arrangement may be the same as that of FIG. 1, however, the drawings of FIG. 2 have been simplified. FIG. 2A shows a clean dressing newly installed in the wound 10 and without any exudate being taken up; FIG. 2B shows the wound contacting element 14 partially full of exudate; and, FIG. 2C shows the wound contacting element 14 saturated with wound exudate. However, the nature of the wound contacting element material 14 is such that no liquid is aspirated by the vacuum connection tube 28 out of the wound cavity 24 or indeed out of the wound contacting element 14 itself.

Figure 3:
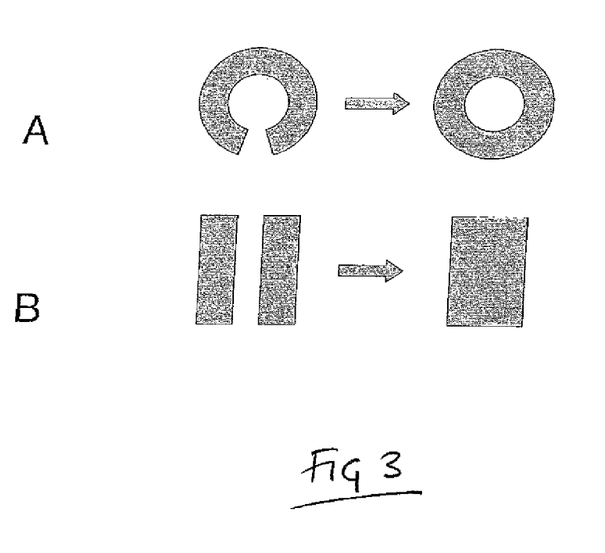
FIG. 3 illustrates a liquid contact triggered valve.

FIG. 3 shows paradigms of the conversion of a first stable physical geometry into a second stable physical geometry upon hydration, wherein hydration enables the self-coalescence (fusion) of spatially separated elements of the first stable physical geometry. In case A, the self-coalescence comprises the fusion of spatially separated surfaces of a single element; in case B the surfaces are adjacent surfaces of two separate elements.

The Examples described below are based on the use of the apparatus arrangement shown in FIG. 1 and/or FIG. 2 and/or FIG. 3.

Example 1

Application of apparatus of FIG. 1 to ex vivo cavity wound. A 5 cm diameter, 5 cm depth cavity wound was cut by scalpel into a porcine leg joint. The musculature in the area of the wound cavity was injected with saline to ensure that the tissue was adequately hydrated for the duration of the experiment. The wound cavity was packed with two wound contacting elements of non-woven balls of carboxymethylchitosan fibre and the wound cavity and filling was covered over with an adhesive silicone gel sheet Cica-Care (trade mark) made by Smith & Nephew Medical Ltd with a central 5 mm diameter aperture 20. A luer loc fitting attached to a coiled vacuum hose was inserted through the aperture and connected to a battery-powered vacuum source Pac-Vac (trade mark) made by Virtual Industries Inc. Immediate contraction of the wound margin was observed and the non-woven balls were compressed down to be flush with the surface of the skin. The system was left in place for 8 hours undisturbed, after which time no fluid had exited the cavity packing but had collected within it.

Example 2

Assembly of apparatus based on FIG. 1 having a wound covering element 14 of Allevyn Adhesive (trade mark) made by Smith & Nephew Medical Ltd.

A 3 mm diameter aperture in the top film of Allevyn Adhesive was created using a biopsy punch. Over this aperture was bonded a silicone elastomer dome miniValve (trade mark) made by Mini Valve International B. V., part number DO 072.004. A miniature vacuum source made by Virtual Industries Inc., PAC-VAC V3200 (trade mark) was coupled by vacuum tubing 28 to a hand-made silicone rubber cup 30.

Example 3

Usage of apparatus based on Allevyn Adhesive as in Example 2. A 5 cm diameter, 5 cm depth cavity wound was cut by scalpel into a porcine leg joint. The musculature in the area of the wound cavity was injected with saline to ensure that the tissue was adequately hydrated for the duration of the experiment. The wound cavity was packed with wound contacting element 14 comprising two non-woven balls of carboxymethylchitosan fibre and the wound cavity 24 and filling was covered over with the modified Allevyn Adhesive dressing described in Example 2. The vacuum source, as described in Example 2, was turned on and the vacuum tubing cup placed over the dome valve positioned centrally on the Allevyn Adhesive. Immediate contraction of the Allevyn Adhesive dressing and the wound margin was observed and the non-woven balls were compressed down to be flush with the surface of the skin. The system was left in place for 8 hours undisturbed, after which time no fluid had exited the cavity packing but had collected within it.

Example 4

Usage of apparatus based on Allevyn Adhesive as described in Example 2. A 5 cm diameter, 5 mm depth shallow wound was cut by scalpel into a porcine leg joint. The musculature in the area of the wound was injected with saline to ensure that the tissue was adequately hydrated for the duration of the experiment. The wound was covered with a non-woven sheet of carboxymethylchitosan as the wound contacting element 14 and the wound and non-woven sheet was covered over with the modified Allevyn Adhesive dressing described in Example 2 as the wound covering element 18. The vacuum source, as described in Example 2, was turned on and the vacuum tubing cup placed over the dome valve positioned centrally on the Allevyn Adhesive. Immediate contraction of the Allevyn Adhesive dressing was observed. The system was left in place for 8 hours undisturbed, after which time no fluid had exited the wound dressing but had collected within it.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:
1. An apparatus for the application of topical negative pressure therapy to a wound, the apparatus comprising:

a wound covering element configured to be positioned over the wound, wherein the wound covering element comprises an aperture;

a vacuum connection conduit configured to be connected to the wound covering element; and, a wound dressing portion comprising an absorbent material configured to be placed over the wound and under the wound covering element, the absorbent material configured to retain wound exudate therein upon application of negative pressure; and a self-coalescing liquid blocking material positioned at the aperture in the wound covering element, wherein the liquid blocking material is configured to inhibit wound exudate from being aspirated into the vacuum connection conduit.

2. The apparatus of claim 1, wherein the liquid blocking material comprises a valve that closes upon contact with wound exudate and blocks all liquid transport beyond itself away from the wound site, the valve being open prior to contact with wound exudate.

3. The apparatus of claim 1, wherein the wound dressing portion and the wound covering element form a single element.

4. The apparatus of claim 1, wherein the absorbent material comprises a superabsorbent material.

5. The apparatus of claim 1, wherein the absorbent material comprises a non-woven material.

6. The apparatus of claim 1, wherein the absorbent material comprises a knit or woven material.

7. The apparatus of claim 1, wherein the wound covering element additionally comprises an adhesive for adhering to a portion of skin surrounding the wound.

8. The apparatus of claim 1, further comprising a vacuum source configured to provide vacuum to the vacuum connection conduit.

9. An apparatus for the application of topical negative pressure therapy to a wound site, the apparatus comprising:

an absorbent wound contacting element for retaining wound exudate fluid therein;

a wound covering element configured to provide a substantially airtight seal over the wound contacting element and the wound site;

an absorbent material that transforms into a gel upon contact with wound exudate fluid positioned in or over an aperture in the wound covering element; and a vacuum connection conduit configured to deliver vacuum through the aperture in the wound covering element;

wherein the wound contacting element and the wound covering element are combined into a single element.

10. The apparatus of claim 9, wherein the absorbent material comprises a self-coalescing material.

11. The apparatus of claim 10, wherein the absorbent material comprises self-coalescing fibers.

12. The apparatus of claim 9, wherein the absorbent material is sealed to the wound covering element at the aperture in the wound covering element.

13. The apparatus of claim 9, wherein the absorbent wound contacting element comprises carboxymethylcellulose.

14. The apparatus of claim 9, wherein the absorbent wound contacting element comprises a superabsorbent material capable of self-coalescence upon fluid absorption.

15. The apparatus of claim 9, wherein the absorbent wound contacting element includes dispersions of superabsorbent particles within a network of wicking fibers.

16. The apparatus of claim 9, wherein the wound covering element is substantially impermeable to the flow of liquid, but is substantially permeable to the transmission of water vapor.

17. The apparatus of claim 9, wherein the wound covering element is a transparent polyurethane.

18. The apparatus of claim 9, wherein the wound covering element comprises an absorbent foam.

19. The apparatus of claim 9, further comprising a vacuum source connectable to a distal end of the vacuum connection conduit.

20. The apparatus of claim 19, wherein the vacuum source is mechanically powered by a compressed spring.

21. The apparatus of claim 19, wherein the vacuum source is electrically powered.

22. The apparatus of claim 9, wherein the wound contacting element, the wound covering element and the vacuum connection conduit are combined into a single element.

* * * * *

UNITED STATES PATENT AND TRADEMARK OFFICE
CERTIFICATE OF CORRECTION

PATENT NO. : 9,962,474 B2  
APPLICATION NO. : 14/254807  
DATED : May 8, 2018  
INVENTOR(S) : Bryan Greener Page 1 of 1

It is certified that error appears in the above-identified patent and that said Letters Patent is hereby corrected as shown below:

On the Title Page

In Column 2 (item (56)) at Line 4, Under Other Publications, change "etal.," to --et al.,--.

In the Specification

In Column 5 at Line 34, Change "and or" to --and/or--.

In Column 11 at Line 21, After "ethanol" insert --.--.

In Column 11 at Line 40-43, Delete "The pressure is preferably less than 500 mbar, more preferably less than 1000 mbar. The duration of the drying process, when achieved by vacuum drying, preferably exceeds 8 hours, more preferably exceeding 12 hours." and insert the same on Column 11, Line 39, as a continuation of the same paragraph.

In Column 11 at Line 64, Change "chlorhexidene," to --chlorhexidine,--.

In Column 15 at Line 50, Change "loc" to --lock--.

In Column 15-16 at Line 65-67 (Column 15) 1-5 (Column 16), Delete "A 3 mm diameter aperture in the top film of Allevyn Adhesive was created using a biopsy punch. Over this aperture was bonded a silicone elastomer dome miniValve (trade mark) made by Mini Valve International B. V., part number DO 072.004. A miniature vacuum source made by Virtual Industries Inc., PAC-VAC V3200 (trade mark) was coupled by vacuum tubing 28 to a hand-made silicone rubber cup 30" and insert the same on Column 15, Line 64, as a continuation of the same paragraph.

Signed and Sealed this  
Thirteenth Day of November, 2018

Andrei Iancu  
*Director of the United States Patent and Trademark Office*